US010836717B2

United States Patent
Zhou et al.

(10) Patent No.: US 10,836,717 B2
(45) Date of Patent: Nov. 17, 2020

(54) REAGENTS FOR FLUOROSULFATING ALCOHOLS OR AMINES

(71) Applicants: BIODURO, LLC, San Diego, CA (US); PFIZER, INC., New York, NY (US)

(72) Inventors: Hua Zhou, Shanghai (CN); Paramita Mukherjee, Groton, CT (US); Rongqiang Liu, Kendall Park, NJ (US); Christopher W. Am Ende, Mystic, CT (US); Tianjing Deng, San Diego, CA (US)

(73) Assignees: BioDuro, LLC, San Diego, CA (US); Pfizer Inc., New York, NY (US)

( * ) Notice: Subject to any disclaimer, the term of this patent is extended or adjusted under 35 U.S.C. 154(b) by 0 days.

(21) Appl. No.: 16/103,824

(22) Filed: Aug. 14, 2018

(65) Prior Publication Data

US 2019/0047950 A1  Feb. 14, 2019

Related U.S. Application Data

(60) Provisional application No. 62/545,028, filed on Aug. 14, 2017, provisional application No. 62/590,930, filed on Nov. 27, 2017, provisional application No. 62/591,725, filed on Nov. 28, 2017.

(51) Int. Cl.

| | | |
|---|---|---|
| C07C 303/24 | (2006.01) | |
| C07C 305/26 | (2006.01) | |
| C07C 381/00 | (2006.01) | |
| C07B 45/00 | (2006.01) | |
| C07D 311/16 | (2006.01) | |
| C07D 491/10 | (2006.01) | |
| C07D 213/65 | (2006.01) | |
| C07D 413/04 | (2006.01) | |
| C07C 227/10 | (2006.01) | |
| C07C 307/00 | (2006.01) | |
| C07D 239/88 | (2006.01) | |
| C07D 215/32 | (2006.01) | |
| C07D 211/96 | (2006.01) | |
| C07D 209/88 | (2006.01) | |
| C07D 249/18 | (2006.01) | |

(52) U.S. Cl.
CPC ............ *C07C 381/00* (2013.01); *C07B 45/00* (2013.01); *C07C 227/10* (2013.01); *C07C 303/24* (2013.01); *C07C 305/26* (2013.01); *C07C 307/00* (2013.01); *C07D 209/88* (2013.01); *C07D 211/96* (2013.01); *C07D 213/65* (2013.01); *C07D 215/32* (2013.01); *C07D 239/88* (2013.01); *C07D 249/18* (2013.01); *C07D 311/16* (2013.01); *C07D 413/04* (2013.01); *C07D 491/10* (2013.01)

(58) Field of Classification Search
CPC ............................. C07C 305/26; C07C 307/00
See application file for complete search history.

(56) References Cited

U.S. PATENT DOCUMENTS

2014/0234696 A1\* 8/2014 Sakuma ............ H01M 10/0566
429/163

FOREIGN PATENT DOCUMENTS

WO   2015188120 A1   12/2015

OTHER PUBLICATIONS

International Search Report and Written Opinion issued in PCT/US2018/046776 dated Oct. 24, 2018.
"Pubchem CID 87968086". Create Date Feb. 12, 2015, Date Accessed: Oct. 8, 2018, 10 pages.
Zhou et al., Introduction of a Crystalline, Shelf-Stable Reagent for the Synthesis of Sulfur(VI) Fluorides. Org Lett. Feb. 2, 2018;20(3):812-815.

\* cited by examiner

*Primary Examiner* — Susanna Moore

(74) *Attorney, Agent, or Firm* — Knobbe, Martens, Olson & Bear LLP

(57) ABSTRACT

Disclosed herein are compounds of formula Ar—N(SO$_2$F)$_2$, wherein Ar is selected from an optionally substituted aryl, an optionally substituted five-membered heteroaryl, or an optionally substituted six-membered heteroaryl. Also disclosed are methods of synthesizing the above compounds by reacting a compound of formula Ar—NH—R$_9$ with MN(SO$_2$F)$_2$.

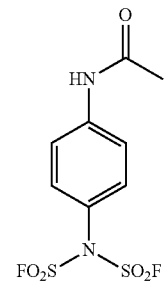

10 Claims, No Drawings

REAGENTS FOR FLUOROSULFATING ALCOHOLS OR AMINES

RELATED APPLICATIONS

The present application claims priority to U.S. Provisional Application Ser. No. 62/545,028, filed on Aug. 14, 2017; to U.S. Provisional Application Ser. No. 62/590,930, filed on Nov. 27, 2017; and to U.S. Provisional Application Ser. No. 62/591,725, filed on Nov. 28, 2017, the entire disclosure of each of which is incorporated by reference herein.

FIELD OF THE INVENTION

The present invention is in the field of novel regents for chemical synthesis and methods of using the same.

BACKGROUND OF THE DISCLOSURE

Sulfuryl gas, $SO_2F_2$, has been used extensively in organic synthesis to synthesize fluorosulfate compounds from alcohols or sulfamoyl fluorides from amines. The use of the gas in these synthetic steps is quite inconvenient. The sulfuryl gas requires specialized equipment, specialized skill, and onerous reaction conditions that add up to limit the use of the gas in chemical synthesis. As the result, a more practical reagent for flurosulfating alcohols and/or amines is needed.

SUMMARY OF THE INVENTION

Disclosed herein are compounds of formula Ar—N(SO$_2$F)$_2$, wherein Ar is selected from an optionally substituted aryl, an optionally substituted five-membered heteroaryl, or an optionally substituted six-membered heteroaryl. Also disclosed are methods of synthesizing the above compounds by reacting a compound of formula Ar—NH—R$_9$ with MN(SO$_2$F)$_2$.

DETAILED DESCRIPTION OF THE EMBODIMENTS

The present inventors have created new reagents for organic synthesis. These reagents efficiently and elegantly result in fluorsulfate compounds without the use of a gas or any specialized equipment. The reagents disclosed herein add a —SO$_2$F group to alcohols or amines. When an alcohol is a starting material, the resulting compound is a fluorosulfate compound. But when an amine is a starting material, the resulting compound is a sulfamoyl fluoride. Both reactions are generally referred to herein as "flurosulfating reactions."

Thus, in one aspect, disclosed herein are compounds of Formula I:

Ar—N(SO$_2$F)$_2$ (I)

wherein Ar is selected from an optionally substituted aryl, an optionally substituted five-membered heteroaryl, or an optionally substituted six-membered heteroaryl.

Unless otherwise indicated, when a substituent is deemed to be "optionally substituted" it is meant that the substituent is a group that may be substituted with one or more group(s) individually and independently selected, without limitation, from alkyl, alkenyl, alkynyl, cycloalkyl, aryl, heteroaryl, heteroalicyclic, hydroxyl, alkoxy, aryloxy, mercapto, alkylthio, arylthio, cyano, halo, perhaloalkyl, carbonyl, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, silyl, trihalomethanesulfonyl, and amino, including mono- and di-substituted amino groups, and the protected derivatives thereof. The protecting groups that may form the protective derivatives of the above substituents are known to those of skill in the art and may be found in references such as Greene and Wuts, Protective Groups in Organic Synthesis, 3$^{rd}$ Ed., John Wiley & Sons, New York, N.Y., 1999, which is incorporated herein in its entirety.

As used herein, "aryl" refers to a carbocyclic (all carbon) ring that has a fully delocalized pi-electron system. The "aryl" group can be made up of two or more fused rings (rings that share two adjacent carbon atoms). When the aryl is a fused ring system, then the ring that is connected to the rest of the molecule has a fully delocalized pi-electron system. The other ring(s) in the fused ring system may or may not have a fully delocalized pi-electron system. Examples of aryl groups include, without limitation, benzene, naphthalene and azulene.

As used herein, "heteroaryl" refers to a ring that has a fully delocalized pi-electron system and contains one or more heteroatoms selected from the group consisting of nitrogen, oxygen, and sulfur in the ring. The "heteroaryl" group can be made up of two or more fused rings (rings that share two adjacent carbon atoms). When the heteroaryl is a fused ring system, then the ring that is connected to the rest of the molecule has a fully delocalized pi-electron system. The other ring(s) in the fused ring system may or may not have a fully delocalized pi-electron system. Examples of heteroaryl rings include, without limitation, furan, thiophene, phthalazinone, pyrrole, oxazole, thiazole, imidazole, pyrazole, isoxazole, isothiazole, triazole, thiadiazole, pyran, pyridine, pyridazine, pyrimidine, pyrazine and triazine.

Wherever "hetero" is used it is intended to mean a group as specified, such as an alkyl or an aryl group, where at least one carbon atom has been replaced with a heteroatom selected from nitrogen, oxygen and sulfur.

As used herein, "alkyl" refers to a straight or branched chain fully saturated (no double or triple bonds) hydrocarbon group. An alkyl group of this invention may comprise from 1 to 20 carbon atoms, that is, m=1 and n=20. An alkyl group herein may also be of medium size having 1 to 10 carbon atoms. An alkyl group herein may also be a lower alkyl having 1 to 5 carbon atoms. Examples of alkyl groups include, without limitation, methyl, ethyl, n-propyl, isopropyl, n-butyl, iso-butyl, sec-butyl, tert-butyl, amyl, tert-amyl, hexyl, heptyl, octyl, nonyl, decyl, undecyl and dodecyl.

An alkyl group of this invention may be substituted or unsubstituted. When substituted, the substituent group(s) can be one or more group(s) independently selected from cycloalkyl, aryl, heteroaryl, heteroalicyclyl, hydroxy, protected hydroxyl, alkoxy, aryloxy, mercapto, alkylthio, arylthio, cyano, halogen, carbonyl, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, silyl, trihalomethanesulfonyl, —NR$^a$R$^b$ and protected amino.

As used herein, "alkenyl" refers to an alkyl group that contains in the straight or branched hydrocarbon chain one or more double bonds. An alkenyl group of this invention may be unsubstituted or substituted. When substituted, the substituent(s) may be selected from the same groups disclosed above with regard to alkyl group substitution, or with regard to optional substitution.

As used herein, "alkynyl" refers to an alkyl group that contains in the straight or branched hydrocarbon chain one or more triple bonds. An alkynyl group of this invention may be unsubstituted or substituted. When substituted, the substituent(s) may be selected from the same groups disclosed above with regard to alkyl group substitution, or with regard to optional substitution.

As used herein, "acyl" refers to an "RC(=O)—" group with R as defined above.

As used herein, "cycloalkyl" refers to a completely saturated (no double bonds) hydrocarbon ring. Cycloalkyl groups of this invention may range from $C_3$ to $C_8$. A cycloalkyl group may be unsubstituted or substituted. If substituted, the substituent(s) may be selected from those indicated above with regard to substitution of an alkyl group. The "cycloalkyl" group can be made up of two or more fused rings (rings that share two adjacent carbon atoms). When the cycloalkyl is a fused ring system, then the ring that is connected to the rest of the molecule is a cycloalkyl as defined above. The other ring(s) in the fused ring system may be a cycloalkyl, a cycloalkenyl, an aryl, a heteroaryl, or a heteroalicyclic.

As used herein, "cycloalkenyl" refers to a cycloalkyl group that contains one or more double bonds in the ring although, if there is more than one, they cannot form a fully delocalized pi-electron system in the ring (otherwise the group would be "aryl," as defined herein). A cycloalkenyl group of this invention may unsubstituted or substituted. When substituted, the substituent(s) may be selected from the same groups disclosed above with regard to alkyl group substitution. The "cycloalkenyl" group can be made up of two or more fused rings (rings that share two adjacent carbon atoms). When the cycloalkenyl is a fused ring system, then the ring that is connected to the rest of the molecule is a cycloalkenyl as defined above. The other ring(s) in the fused ring system may be a cycloalkyl, a cycloalkenyl, an aryl, a heteroaryl, or a heteroalicyclic.

The term "alkylene" refers to an alkyl group, as defined herein, which is a biradical and is connected to two other moieties. Thus, methylene (—$CH_2$—), ethylene (—$CH_2CH_2$—), proylene (—$CH_2CH_2CH_2$—), isopropylene (—$CH_2$—CH($CH_3$)—), and isobutylene (—$CH_2$—CH($CH_3$)—$CH_2$—) are examples, without limitation, of an alkylene group. Similarly, the term "cycloalkylene" refers to a cycloalkyl group, as defined here, which binds in an analogous way to two other moieties. If the alkyl and cycloalkyl groups contain unsaturated carbons, the terms "alkenylene" and "cycloalkenylene" are used.

As used herein, "heterocycloalkyl," "heteroalicyclic," or "heteroalicyclyl" refers to a ring having in the ring system one or more heteroatoms independently selected from nitrogen, oxygen and sulfur. The ring may also contain one or more double bonds provided that they do not form a fully delocalized pi-electron system in the rings. The ring defined herein can be a stable 3- to 18-membered ring that consists of carbon atoms and from one to five heteroatoms selected from the group consisting of nitrogen, oxygen, and sulfur. Heteroalicyclyl groups of this invention may be unsubstituted or substituted. When substituted, the substituent(s) may be one or more groups independently selected from the group consisting of halogen, hydroxy, protected hydroxy, cyano, nitro, alkyl, alkoxy, acyl, acyloxy, carboxy, protected carboxy, amino, protected amino, carboxamide, protected carboxamide, alkylsulfonamido and trifluoromethanesulfonamido. The "heterocycloalkyl" group can be made up of two or more fused rings (rings that share two adjacent carbon atoms). When the heterocycloalkyl is a fused ring system, then the ring that is connected to the rest of the molecule is a heterocycloalkyl as defined above. The other ring(s) in the fused ring system may be a cycloalkyl, a cycloalkenyl, an aryl, a heteroaryl, or a heteroalicyclic.

An "O-carboxy" group refers to a "RC(=O)O—" group with R as defined above.

A "C-carboxy" group refers to a "—C(=O)R" group with R as defined above.

A "perhaloalkyl" group refers to an alkyl group where all of the hydrogen atoms are replaced by a halogen atom. In some embodiments, all the halogens are the same, while in other embodiments, the scope includes alkyl groups having different halogen atoms. Examples of perhaloalkyls include, but are not limited to, trifluoromethyl, pentafluoroethyl, difluorochloromethly, and the like.

An "acetyl" group refers to a $CH_3C$(=O)— group.

A "trihalomethanesulfonyl" group refers to an "$X_3CSO_2$—" group wherein X is a halogen.

A "cyano" group refers to a "—CN" group.

An "isocyanato" group refers to an "—NCO" group.

A "thiocyanato" group refers to a "—CNS" group.

An "isothiocyanato" group refers to an "—NCS" group.

A "sulfinyl" group refers to an "—S(=O)—R" group with R as defined above.

A "sulfonyl" group refers to an "$SO_2R$" group with R as defined above.

An "S-sulfonamido" group refers to a "—$SO_2NR^aR^b$" group with $R^a$ and $R^b$ as defined above.

An "N-sulfonamido" group refers to a "$RSO_2N(R^a)$—" group with R and $R^a$ as defined above.

A "trihalomethanesulfonamido" group refers to an "$X_3CSO_2N(R)$—" group with X as halogen and R as defined above.

An "O-carbamyl" group refers to a "—OC(=O)$NR^aR^b$" group with $R^a$ and $R^b$ as defined above.

An "N-carbamyl" group refers to an "ROC(=O)$NR^a$—" group with $R^a$ and R as defined above.

An "O-thiocarbamyl" group refers to a "—OC(=S)—$NR^aR^b$" group with $R^a$ and $R^b$ as defined above.

An "N-thiocarbamyl" group refers to an "ROC(=S)$NR^a$—" group with $R^a$ and R as defined above.

A "C-amido" group refers to a "—C(=O)$NR^aR^b$" group with $R^a$ and $R^b$ as defined above.

An "N-amido" group refers to a "RC(=O)$NR^a$—" group with R and $R^a$ as defined above.

The term "perhaloalkyl" refers to an alkyl group in which all the hydrogen atoms are replaced by halogen atoms.

As used herein, an "ester" refers to a "—C(=O)OR" group with R as defined above.

As used herein, an "amide" refers to a "—C(=O)$NR^aR^b$" group with $R^a$ and $R^b$ as defined above.

Any unsubstituted or monosubstituted amine group on a compound herein can be converted to an amide, any hydroxyl group can be converted to an ester and any carboxyl group can be converted to either an amide or ester using techniques well-known to those skilled in the art (see, for example, Greene and Wuts, Protective Groups in Organic Synthesis, 3$^{rd}$ Ed., John Wiley & Sons, New York, N.Y., 1999).

As used herein, when two substituents taken together, along with the nitrogen atom to which they are attached, form a heterocycloalkyl or a heteroaryl group, it is meant that the groups may be joined to form a, heteroaryl or heteroalicyclyl group. For example, without limitation, if $R^a$ and $R^b$ of an $NR^aR^b$ group are indicated that taken together, along with the nitrogen atom to which they are attached, form a heterocycloalkyl or a heteroaryl group, it is meant that they are covalently bonded to one another at their terminal atoms to form a ring, such that

forms a

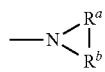

As used herein, when two geminal substituents taken together, along with the carbon atom to which they are attached, form a carbonyl group, it is meant that, for example,

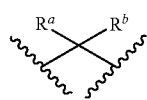

forms a

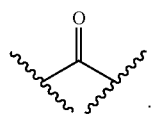 [SMILES: *C(*)=O]

As used herein, when two geminal substituents taken together, along with the carbon atom to which they are attached, form a cycloalkyl or a heterocycloalkyl group, it is meant that, for example,

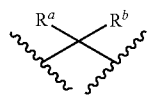

forms a

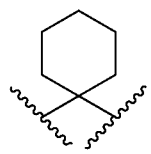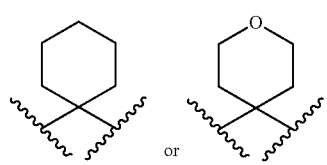

As used herein, when two substituents on adjacent carbons taken together, along with the two intervening carbon atoms to which they are attached, form a double bond, it is meant that, for example,

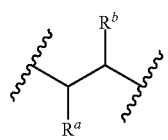

forms a

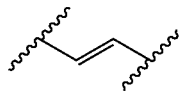 [SMILES: */C=C/*]

which may form a cis, trans, E, or Z double bond.

As used herein, when two substituents on adjacent carbons taken together, along with the two intervening carbon atoms to which they are attached, form a cycloalkyl or a heterocycloalkyl group, or when one substituent and the carbon atom to which it is attached and the carbon atom to which one adjacent substituent is attached, form a cycloalkyl or a heterocycloalkyl group, it is meant that, for example,

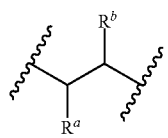

forms a

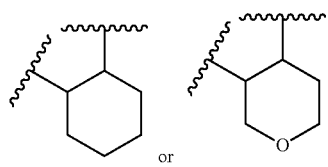

As used herein, when two substituents taken together, along with the carbon atoms to which they are attached and the at least two intervening carbon atoms, form a cycloalkyl or a heterocycloalkyl group, or when one substituent and the carbon atom to which it is attached and the carbon atom to which one non-adjacent substituent is attached, taken together with all intervening carbon atoms, form a cycloalkyl or heterocycloalkyl group, it is meant that, for example,

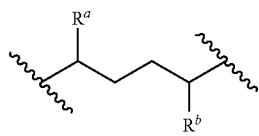

forms a

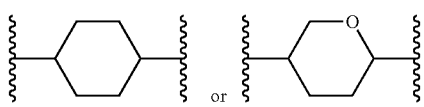

It is understood that, in any compound of this invention having one or more chiral centers, if an absolute stereochemistry is not expressly indicated, then each center may independently be R or S or a mixture thereof. In addition it is understood that, in any compound of this invention having one or more double bond(s) generating geometrical isomers that can be defined as E or Z each double bond may independently be E or Z, or a mixture thereof.

Throughout the present disclosure, when a particular compound comprises a chiral center, the scope of the present disclosure also includes compositions comprising the racemic mixture of the two enantiomers, as well as compositions comprising each enantiomer individually substantially free of the other enantiomer. Thus, for example, contemplated herein is a composition comprising the S enantiomer substantially free of the R enantiomer, or a composition comprising the R enantiomer substantially free of the S enantiomer. By "substantially free" it is meant that the composition comprises less than 10%, or less than 8%, or less than 5%, or less than 3%, or less than 1% of the minor enantiomer. If the particular compound comprises more than one chiral center, the scope of the present disclosure also includes compositions comprising a mixture of the various diastereomers, as well as compositions comprising each diastereomer substantially free of the other diastereomers. The recitation of a compound, without reference to any of its particular diastereomers, includes compositions comprising all four diastereomers, compositions comprising the racemic mixture of R,R and S,S isomers, compositions comprising the racemic mixture of R,S and S,R isomers, compositions comprising the R,R enantiomer substantially free of the other diastereomers, compositions comprising the S,S enantiomer substantially free of the other diastereomers, compositions comprising the R,S enantiomer substantially free of the other diastereomers, and compositions comprising the S,R enantiomer substantially free of the other diastereomers.

In some embodiments, Ar of Formula I is a moiety of Formula II:

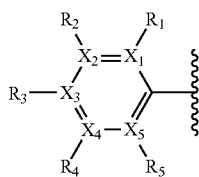

wherein:
each $X_1$-$X_5$ is independently carbon or nitrogen,
wherein when any of $X_1$-$X_5$ is nitrogen, the corresponding R group is null, and
wherein none, one, two, or three of $X_1$-$X_5$ are nitrogen;
each of $R_1$-$R_5$ is each independently selected from hydrogen, halide, an optionally substituted alkyl, an optionally substituted aryl, an optionally substituted five-membered heteroaryl, or an optionally substituted six-membered heteroaryl; or a moiety of formula $R_6$—X—C(=O)—$NR_7$—,
X is selected from a bond, oxygen, or —$NR_8$,
wherein $R_6$-$R_8$ is each independently selected from hydrogen, an optionally substituted alkyl, an optionally substituted aryl, an optionally substituted five-membered heteroaryl, or an optionally substituted six-membered heteroaryl,
$R_1$ and $R_2$, or $R_2$ and $R_3$, or $R_3$ and $R_4$, or $R_4$ and $R_5$, taken together with the carbon atoms to which they are attached, form an optionally substituted aryl, an optionally substituted five-membered heteroaryl, an optionally substituted six-membered heteroaryl, or;
In some embodiments, each of $R_1$, $R_2$, $R_4$, and $R_5$ is independently selected from hydrogen, halide, an optionally substituted alkyl, an optionally substituted aryl, an optionally substituted five-membered heteroaryl, or an optionally substituted six-membered heteroaryl. In other embodiments, each of $R_1$, $R_2$, $R_4$, and $R_5$ is independently selected from hydrogen, fluoro, chloro, bromo, methyl, trifluoromethyl, ethyl, perfluoroethyl, n-propyl, i-propyl, n-butyl, sec-butyl, or tert-butyl. In still other embodiments, each of $R_1$, $R_2$, $R_4$, and $R_5$ is independently selected from hydrogen, chloro, methyl, trifluoromethyl, and ethyl. In further embodiments, $R_1$, $R_2$, $R_4$, and $R_5$ are hydrogen.

In some embodiments, $R_3$ is a moiety of formula $R_6$—C(=O)—NH—.

In some embodiments, one of $X_1$-$X_5$ is nitrogen, whereas in other embodiments, all of $X_1$-$X_5$ are carbon.

In some embodiments, $R_6$ is independently selected from hydrogen, methyl, ethyl, n-propyl, i-propyl, n-butyl, sec-butyl, or tert-butyl. In other embodiments, $R_6$ is independently selected from methyl, ethyl, and n-propyl. In certain embodiments, $R_6$ is methyl.

In some embodiments, the compound of Formula I is (4-acetamidophenyl)(fluorosulfonyl)sulfamoyl fluoride, also termed [4-(acetylamino)phenyl]imidodisulfuryl difluoride (AISF), which is the compound of Formula III:

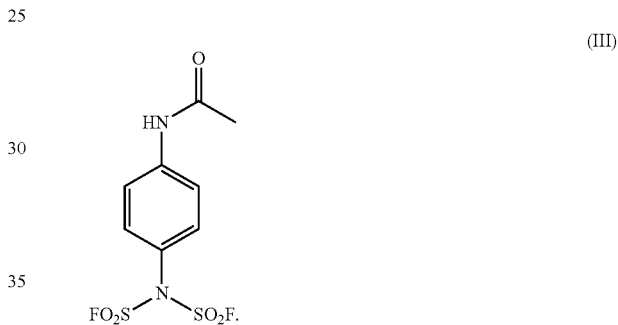

In another aspect, disclosed herein are methods of synthesizing a compound of Formula I, as described above, the method comprising the step of reacting a compound of Formula IV with $MN(SO_2F)_2$, according to Scheme I, to obtain a compound of Formula V:

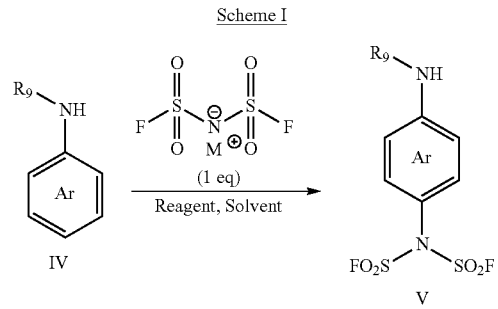

wherein:
Ar is an aromatic group as defined above (even though Ar is shown as a phenyl derivative in Scheme I, the ordinary artisan understands that Ar can be any of the groups defined as above);
M is a metal ion;
$R_9$ is $R_6$ or $R_6$—X—C(=O)—$NR_7$—.
In some embodiments, the reagent activates an aromatic C—H bond. The ordinary artisan is aware of various reagents that can be used for this reaction. An example of such a reagent is phenyliodonium diacetate, PhI(OAc)$_2$.

In some embodiments, the solvent is an organic solvent that encourages, or at least does not inhibit, the reaction of Scheme I. In certain embodiments, the solvent is a haloalkyl. Examples of the solvent include, but are not limited to, tetrachloromethyl, dichloromethyl, dichloroethyl, and the like.

In some embodiments, M is an alkali metal, whereas in other embodiments, M is an alkali earth metal. In still other embodiments, M is a transition metal. Examples of metal ions that can be used as M include, but are not limited to, the ions of lithium, sodium, potassium, magnesium, copper, silver, iron, palladium, or manganese.

In the above Scheme I, R$_6$ and R$_7$ are as defined previously.

In some embodiments, the reaction is carried out at room temperature, while in other embodiments, the reaction is carried out in temperatures higher than room temperature. In some of these embodiments, the reaction is carried out at reflux.

In another aspect, disclosed herein are methods of synthesizing a fluorosulfate derivative of an alcohol or an amine, the method comprising the step of reacting the alcohol or the amine with a compound of any one of claims 1-13.

In some embodiments, the alcohol is an aromatic alcohol. In certain embodiments, the alcohol is an optionally substituted phenol.

In some embodiments, the amine is an aliphatic amine. In some of these embodiments, the amine is a secondary amine.

In another aspect, disclosed herein are compounds synthesized by the above method.

In another aspect, disclosed herein are fluorosulfate derivatives of an alcohol or an amine synthesized by the above method.

In another aspect, disclosed herein is the use of a compound of Formula I for the synthesis of a fluorosulfate derivative of an alcohol or an amine.

EXAMPLES

Example 1

General Information

Materials. All commercially available chemicals, reagents and solvents were used as received. Lithium bis(fluorosulfonyl)imide (CAS #171611-11-3) was purchased from TCI America, (diacetoxyiodo)benzene (PIDA, CAS#3240-34-4) was purchased from Sigma-Aldrich or Accela. Imidodisulfuryl fluoride lithium salt was obtained from TCI. Iodobenzene diacetate was purchased from Accela. 2,3,4,6,7,8,9,10-octahydropyrimido[1,2-a]azepine (DBU) was purchased from Accela. Triethylamine and potassium carbonate was purchased from Titan. Tetrahydrofuran and dichloromethane were dispensed from a dry solvent system. Chromatography columns were packed with silica gel (40-60 μm, 250-370 mesh) was purchased from Agela. Reactions were monitored by thin layer chromatography (TLC) performed on Analtech, Inc. silica gel GF 250 μm plates or Merck silica gel plates (60 F$_{254}$) and were visualized with ultraviolet (UV) light (254 nm) and/or KMnO$_4$ staining or by UPLC-MS (Waters Acquity, ESCI (ESI+/−, APCI +/−)).

Instrumentation. Proton nuclear magnetic resonance ($^1$H NMR) spectra, carbon nuclear magnetic resonance ($^{13}$C NMR) spectra and $^{19}$F fluorine spectra were recorded on a Bruker 400 AVANCE equipped with a cryoprobe (400, 125 and 376 MHz, respectively). Chemical shifts are reported in ppm relative to chloroform ($^1$H, δ=7.26 and $^{13}$C NMR δ=77.00), methanol ($^1$H, δ=3.31, $^{13}$C NMR δ=49.15), dimethyl sulfoxide ($^1$H, δ=2.50 ppm, $^{13}$C NMR δ=39.51), tetrahydrofuran ($^1$H, δ=1.73 ppm). $^{19}$F fluorine chemical shifts are reported in parts per million and are referenced to CFCl$_3$ (δ 0 ppm). NMR data are represented as follows: chemical shift (δ ppm), multiplicity (s=singlet, d=doublet, t=triplet, q=quartet, p=pentet, hept=heptet, m=multiplet,), coupling constant in Hertz (Hz), integration. All NMR spectra were taken at 25° C. High-performance liquid chromatography (HPLC) was performed on either an Agilent 1260 series instrument with a binary pump and a diode array detector. Liquid chromatography/mass spectrometry (LC-MS) data was obtained on an Agilent 1260 Infinity instrument with a binary pump, a diode array detector, and an Agilent 6120 quadrupole detector, or an Agilent model 6220 MS(TOF). Differential scanning calorimetry was performed on a DSC Q20 V24.10 Build 122 (TA instruments). Infrared (IR) spectra were recorded with a Thermo-Nicolet Avatar 360 FT-IR. High-resolution mass spectra (HRMS) were acquired on. Melting points were recorded on a Sanford Research Systems OptiMelt and are uncorrected. UPLC-MS (Waters Acquity), Column: Waters Acquity HSS T3, 2.1 mm×50 mm, C18, 1.7 μm; Column Temperature 60° C., Mobile Phase: A: 0.1% formic acid in water (v/v); Mobile phase B: 0.1% formic acid in acetonitrile (v/v), Gradient Profiles: Flow—1.25 mL/min, 1.5 min Run: Initial conditions: A-95%:B-5%; hold at initial from 0.0-0.1 min; Linear Ramp to A-5%:B-95% over 0.1-1.0 min; hold at A-5%:B-95% from 1.0-1.1 min; return to initial conditions 1.1-1.5 min, 3.0 min run: Initial conditions: A-95%:B-5%; hold at initial from 0.0-0.1 min; Linear Ramp to A-5%:B-95% over 0.1-2.6 min; hold at A-5%:B-95% from 2.6-2.95 min; return to initial conditions 2.95-3.0 min. Detectors: Waters Acquity PDA; 200-450 nm scan; 1.2 nm interval, Waters Acquity ELS detector; drift tube 65° C., Waters SQ MS(single quad) Tune: ESI-3.5 kV Capillary/APCI (in ESCI mode)-0.3 μA Corona Pin, 30 V Cone, Source 150° C., Desolvation 475° C., Desolvation Gas N2 400 L/hr, MS Methods: ESCI (ESI+/−, APCI+/−), 100-2000 m/z scan, 0.4 sec scan time, Centroid, Injection Volume: 5 μL, System Components: Waters Acquity UPLC (Acquity Binary Solvent Manager, 2777C-Autosampler, Acquity PDA, Acquity ELS and Acquity Column Manager) and Waters Acquity SQ systems from Waters Corporation, Milford, Mass.

Example 2

[4-(Acetylamino)phenyl]imidodisulfuryl difluoride (AISF)

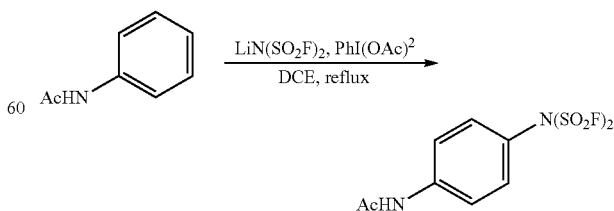

To a refluxing solution of lithium bis(fluorosulfonyl) imide (5.24 g, 27.9 mmol, 2 equiv.) and (diacetoxyiodo)

benzene (7.48 g, 23.2 mmol, 1.5 equiv.) in 1,2-dichloroethane (30 mL) was added acetanilide (2.09 g, 15.5 mmol, 1 equiv.) in 1,2-dichloroethane (35 mL) dropwise over a period of 25 minutes. The mixture was refluxed an additional 15 minutes and then cooled to room temperature and concentrated under reduced pressure. The crude residue was purified by silica gel flash chromatography eluting with 45% EtOAc/heptane to afford a pale amber solid (4.20 g, 86% yield, >95% purity by 1H NMR). The amber solid was dissolved in hot MTBE and activated charcoal (1 g) was added and the mixture was stirred overnight, filtered and concentrated under reduced pressure. The resulting off-white solid was triturated with MTBE/heptane (1:1, 20 mL) to afford the title compound (3.75 g, 77% yield) as a white solid. Physical State: White solid. TLC: $R_f$=0.34 (60% EtOAc/Heptane). $^1$H NMR: (400 MHz, DMSO-$d_6$) δ 10.37 (s, 1H), 7.90-7.63 (m, 4H), 2.09 (s, 3H) ppm. $^{13}$C NMR: (101 MHz, DMSO-$d_6$) δ 169.06, 142.88, 130.26, 126.07, 120.23, 24.10 ppm. $^{19}$F NMR: (376 MHz, DMSO-$d_6$) δ 56.75 (s, 2F) ppm. HRMS: Calculated for $C_8H_8F_2N_2NaO_5S_2$ [M+Na]$^+$336.9740, found 336.9736. IR (neat): v=3322, 1671, 1600, 1525, 1477, 1450, 1411, 1371, 1316 cm$^{-1}$. mp: 141.0-143.1° C.

Alternative procedure: A blast shield was utilized because of the large scale of this reaction. To a refluxing solution of lithium bis(fluorosulfonyl)imide (25.27 g, 134.4 mmol, 2 equiv.) and (diacetoxyiodo)benzene (37.4 g, 116 mmol, 1.5 equiv.) in 1,2-dichloroethane (100 mL) was added acetanilide (10.5 g, 77.5 mmol, 1 equiv.) in 1,2-dichloroethane (180 mL) dropwise over a period of 60 minutes. The mixture was refluxed an additional 30 minutes and then cooled to room temperature. Activated charcoal (8 g) was added and in the mixture was stirred at room temperature for 30 minutes and then the suspension was filtered and concentrated under reduced pressure. The crude residue was resuspended in DMSO (100 mL), water (20 mL) and brine (10 mL) and then extracted with MTBE (4×130 mL). The combined organic fraction was washed with water (2×130 mL) and brine (130 mL), dried with anhydrous magnesium sulfate, filtered and concentrated to a thick slurry. The slurry was diluted with heptane (~50 mL) and stirred on ice for 2 hours and then filtered to afford AISF (14.7 g, 60% yield) as a white solid.

Example 3

General Procedure for the Synthesis of Aryl Fluorosulfates and Sulfamoyl Fluorides

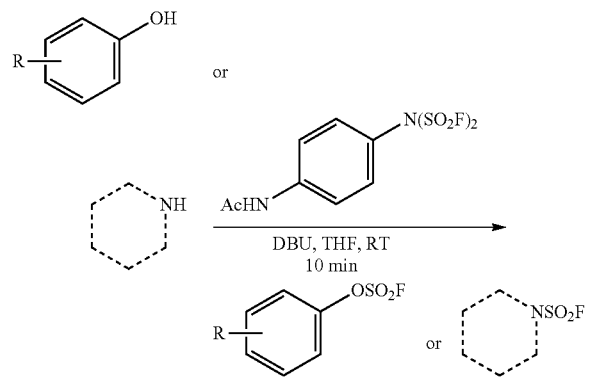

To a 2-dram vial equipped with a magnetic stir bar, the phenol or amine substrate (0.4 mmol) and AFSI (134 mg, 0.48 mmol, 1.2 equiv.), was added tetrahydrofuran (2 mL). 1,8-Diazabicyclo[5.4.0]undec-7-ene (132 μL, 0.88 mmol, 2.2 equiv.) was added to the mixture over a period of 30 seconds. The reaction mixture was stirred at room temperature for 10 minutes and then diluted with ethyl acetate or ether and washed with either 0.5 N KHSO$_4$ or 0.5 N HCl (2×) and brine (1×). The combined organic fraction was dried with anhydrous sodium sulfate and concentrated under reduced pressure. The crude residue was purified by silica gel flash chromatography.

Example 4

4-Benzoylphenyl sulfurofluoridate

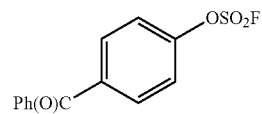

4-Benzoylphenyl sulfurofluoridate was prepared following the general procedure. An average of two independent experiments was used to calculate the yield (97% and 96%, average: 97%). Physical State: White solid, $^1$H NMR: (400 MHz, CDCl$_3$) δ 7.97-7.90 (m, 2H), 7.83-7.77 (m, 2H), 7.68-7.60 (m, 1H), 7.55-7.44 (m, 4H), $^{13}$C NMR: (101 MHz, CDCl$_3$) δ 194.69, 152.24, 137.89, 136.67, 133.08, 132.25, 130.00, 128.56, 120.92, $^{19}$F NMR: (376 MHz, CDCl$_3$) δ 38.76 (s, 1F), MS: (EI) 280.1 [M]+.

Example 5

Ethyl 4-((fluorosulfonyl)oxy)benzoate

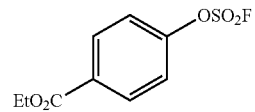

Ethyl 4-((fluorosulfonyl)oxy)benzoate was prepared following the general procedure. An average of two independent experiments was used to calculate the yield (99% and 98%, average: 99%). Physical State: colorless oil, $^1$H NMR: (400 MHz, CDCl$_3$) δ 8.17 (d, J=8.8 Hz, 2 H), 7.41 (d, J=8.7 Hz, 2 H), 4.40 (q, J=7.1 Hz, 2 H), 1.40 (t, J=7.1 Hz, 3 H), $^{13}$C NMR: (101 MHz, CDCl$_3$) δ 164.83, 152.73, 131.96, 130.95, 120.86 (d, J=1.0 Hz), 61.58, 14.22, $^{19}$F NMR: (376 MHz, CDCl$_3$) δ 38.61 (s, 1 F), MS: (EI) 248.0 [M]+.

Example 6

4-Cyanophenyl

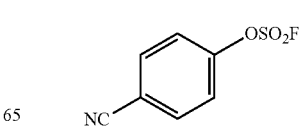

4-Cyanophenyl was prepared following the general procedure. An average of two independent experiments was used to calculate the yield (95% and 99%, average: 97%). Physical State: white solid, $^1$H NMR: (400 MHz, CDCl$_3$) δ 7.83 (d, J=9.0 Hz, 2H), 7.51 (d, J=9.0 Hz, 2H), $^{13}$C NMR: (101 MHz, CDCl$_3$) δ 152.2, 134.7, 122.2, 117.0, 113.2, $^{19}$F NMR: (376 MHz, CDCl$_3$) δ 39.4 (s, 1F), MS: (EI) 201.1 [M]+.

Example 7

4-Phenoxyphenyl sulfurofluoridate

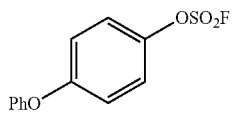

4-Phenoxyphenyl sulfurofluoridate was prepared following the general procedure using 4-phenoxyphenol. An average of two independent experiments was used to calculate the yield (91% and 88%, average: 90%). Physical State: white solid, $^1$H NMR: (400 MHz, CDCl$_3$) δ 7.43-7.36 (m, 2H), 7.33-7.26 (m, 2H), 7.23-7.16 (m, 1H), 7.09-7.01 (m, 4H), $^{13}$C NMR: (101 MHz, CDCl$_3$) δ 157.55, 155.99, 144.86, 130.05, 124.39, 122.25, 119.61, 119.41, $^{19}$F NMR: (376 MHz, CDCl$_3$) δ 36.84 (s, 1F), MS: (EI) 268.1 [M]+.

Example 8

2-Oxo-2H-chromen-7-yl sulfurofluoridate

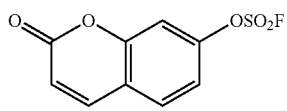

2-Oxo-2H-chromen-7-yl sulfurofluoridate was prepared following the general procedure. An average of two independent experiments was used to calculate the yield (88% and 84%, average: 86%). Physical State: white solid, $^1$H NMR: (400 MHz, CDCl$_3$) δ 7.73 (d, J=9.5 Hz, 1H), 7.62 (d, J=8.6 Hz, 1H), 7.36 (d, J=2.2 Hz, 1H), 7.29 (ddd, J=0.7, 2.4, 8.6 Hz, 1H), 6.51 (d, J=9.8 Hz, 1H), $^{13}$C NMR: (101 MHz, CDCl$_3$) δ 159.15, 154.63, 151.13, 142.04, 129.62, 118.98, 117.90, 117.15, (d, J=1.5 Hz), 110.18, $^{19}$F NMR: (376 MHz, CDCl$_3$) δ 39.04 (s, 1F), MS: (ES-API) 245.0 [M+H]+.

Example 9

4-Formyl-2-methoxyphenyl sulfurofluoridate

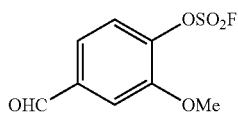

4-Formyl-2-methoxyphenyl sulfurofluoridate was prepared following the general procedure. An average of two independent experiments was used to calculate the yield (98% and 97%, average: 98%). Physical State: colorless oil, $^1$H NMR: (400 MHz, CDCl$_3$) δ 9.99 (s, 1H), 7.58 (s, 1H), 7.54-7.48 (m, 2H), 4.00 (s, 3H), $^{13}$C NMR: (101 MHz, CDCl$_3$) δ 190.30, 152.01, 142.75, 137.03, 123.93, 123.10, 112.07, 56.48, $^{19}$F NMR: (376 MHz, CDCl$_3$) δ 41.00 (s, 1F), MS: (ES-API) 235.1 [M+H]+.

Example 10

3-(Phenylcarbamoyl)phenyl sulfurofluoridate

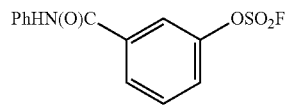

3-(Phenylcarbamoyl)phenyl sulfurofluoridate was prepared following the general procedure using 3-hydroxy-N-phenylbenzamide. An average of two independent experiments was used to calculate the yield (97% and 82%, average: 90%). Physical State: white solid, $^1$H NMR: (400 MHz, CDCl$_3$) δ 7.94-7.87 (m, 2H), 7.75 (br s, 1H), 7.68-7.60 (m, 3H), 7.59-7.53 (m, 1H), 7.44-7.38 (m, 2H), 7.24-7.18 (m, 1H), $^{13}$C NMR: (101 MHz, CDCl$_3$) δ 163.5, 150.1, 137.7, 137.2, 130.9, 129.2, 126.9, 125.2, 124.1, 120.5, 120.2, $^{19}$F NMR: (376 MHz, CDCl$_3$) δ 38.5 (s, 1F), MS: (EI) 295.1 [M]+.

Example 11

6-Methylpyridin-3-yl sulfurofluoridate

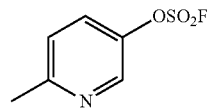

6-Methylpyridin-3-yl sulfurofluoridate was prepared following the general procedure. An average of two independent experiments was used to calculate the yield (94% and 99%, average: 97%). Physical State: colorless oil, $^1$H NMR: (400 MHz, CDCl$_3$) δ 8.54 (d, J=2.8 Hz, 1 H), 7.58 (dd, J=8.6, 2.6 Hz, 1 H), 7.28 (d, J=8.6 Hz, 1 H), 2.62 (s, 3 H), $^{13}$C NMR: (101 MHz, CDCl$_3$) δ 159.38, 145.28, 141.66 (d, J=1.0 Hz), 128.71 (d, J=1.0 Hz), 124.34, 24.02, $^{19}$F NMR: (376 MHz, CDCl$_3$) δ 37.93 (s, 1 F), MS: (ESI) 192.0 [M+H]+.

Example 12

5-Chloroquinolin-8-yl sulfurofluoridate

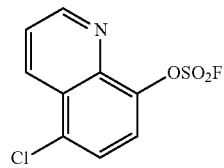

5-Chloroquinolin-8-yl sulfurofluoridate was prepared following the general procedure. An average of two independent experiments was used to calculate the yield (95% and 88%, average: 92%). Physical State: white solid, $^1$H NMR: (400 MHz, CDCl$_3$) δ 9.13 (dd, J=3.9, 1.6 Hz, 1H), 8.65 (dd, J=9.0, 2.0 Hz, 1H), 7.73-7.66 (m, 3H), $^{13}$C NMR: (101 MHz, CDCl$_3$) δ 152.3, 144.7, 140.9, 133.2, 132.0, 127.8, 125.75, 123.4, 121.26, $^{19}$F NMR: (376 MHz, CDCl$_3$) δ 41.0 (s, 1F) ppm, MS: (EI) 261.0 [M]+.

Example 13

Mesityl sulfurofluoridate

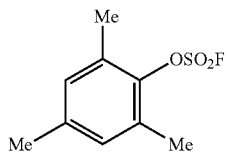

Mesityl sulfurofluoridate was prepared following the general procedure. An average of two independent experiments was used to calculate the yield (80% and 89%, average: 85%). Physical State: colorless oil, $^1$H NMR: (400 MHz, CDCl$_3$) δ 6.93 (s, 2H), 2.35 (s, 6H), 2.30 (s, 3H), $^{13}$C NMR: (101 MHz, CDCl$_3$) δ 148.8, 138.0, 130.4, 130.3, 20.7, 16.4, $^{19}$F NMR: (376 MHz, CDCl$_3$) δ 42.9 (s, 1F), MS: (EI) 218.1 [M]+.

Example 14

4-Aminophenyl sulfurofluoridate

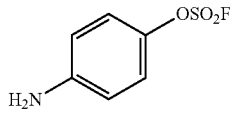

4-Aminophenyl sulfurofluoridate was prepared following the general procedure. An average of two independent experiments was used to calculate the yield (95% and 95%, average: 95%). Physical State: light yellow oil, $^1$H NMR: (400 MHz, CDCl$_3$) δ 7.18-7.01 (m, 2H), 6.76-6.57 (m, 2H), 3.82 (br. s., 2H), $^{13}$C NMR: (101 MHz, CDCl$_3$) δ 146.65, 142.13, 121.78, 115.49, $^{19}$F NMR: (376 MHz, CDCl$_3$) δ 35.97 (s, 1F), MS: (ES-API) 192.1 [M+H]+.

Example 15

4-(Hydroxydiphenylmethyl)piperidine-1-sulfonyl fluoride

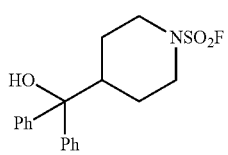

4-(Hydroxydiphenylmethyl)piperidine-1-sulfonyl fluoride was prepared following the general procedure. An average of two independent experiments was used to calculate the yield (98% and 94%, average: 96%). Physical State: white solid, $^1$H NMR: (400 MHz, CDCl$_3$) δ 7.44 (d, J=7.7 Hz, 4 H), 7.33 (t, J=7.7 Hz, 4 H), 7.23 (t, J=7.3 Hz, 2 H), 3.95 (d, J=12.6 Hz, 2 H), 3.02 (t, J=12.5 Hz, 2 H), 2.56 (tt, J=11.5, 3.2 Hz, 1 H), 2.11 (s, 1 H), 1.68-1.54 (m, 4H), $^{13}$C NMR: (101 MHz, CDCl$_3$) δ 144.88, 128.47, 127.06, 125.63, 79.35, 47.61, 43.32, 25.54, $^{19}$F NMR: (376 MHz, CDCl$_3$) δ 39.59 (s, 1 F), MS: (ESI) 332.2 [M−H$_2$O+H]+.

Example 16

4-(2-Chlorodibenzo[b,f][1,4]oxazepin-11-yl)piperazine-1-sulfonyl fluoride

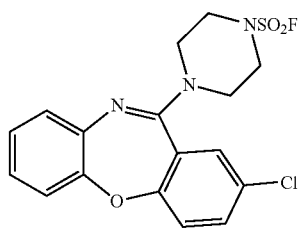

4-(2-Chlorodibenzo[b,f][1,4]oxazepin-11-yl)piperazine-1-sulfonyl fluoride was prepared following the general procedure. An average of two independent experiments was used to calculate the yield (96% and 89%, average: 93%). Physical State: white solid, $^1$H NMR: (400 MHz, CDCl$_3$) δ 7.44 (d, J=8.6 Hz, 1 H), 7.31 (s, 1 H), 7.25-7.04 (m, 5 H), 3.67 (s, 4 H), 3.59 (s, 4 H), $^{13}$C NMR: (101 MHz, CDCl$_3$) δ 159.42, 158.25, 151.67, 139.35, 133.14, 130.64, 128.59, 127.15, 125.93, 125.46, 124.42, 122.99, 120.24, 46.53, 46.40, $^{19}$F NMR: (376 MHz, CDCl$_3$) δ 39.24 (s, 1 F), MS: (ESI) 396.1 [M+H]+.

Example 17

(2,2-Dimethoxyethyl)(methyl)sulfamoyl fluoride

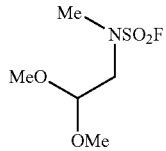

(2,2-Dimethoxyethyl)(methyl)sulfamoyl fluoride was prepared following the general procedure. An average of two independent experiments was used to calculate the yield (80% and 73%, average: 77%). Physical State: colorless oil, $^1$H NMR: (400 MHz, CDCl$_3$) δ 4.53 (t, J=5.4 Hz, 1H), 3.44 (s, 6H), 3.38 (dd, J=2.0, 5.4 Hz, 2H), 3.12 (d, J=2.2 Hz, 3H), $^{13}$C NMR: (101 MHz, CDCl$_3$) δ 103.00 (d, J=2.2 Hz, 1C), 55.02, 52.80 (d, J=2.2 Hz, 1C), 37.92 (d, J=1.5 Hz, 1C), $^{19}$F NMR: (376 MHz, CDCl$_3$) δ 43.44 (s, 1F).

Example 18

1,4-Dioxa-8-azaspiro[4.5]decane-8-sulfonyl fluoride

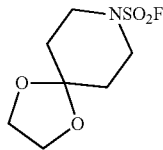

1,4-Dioxa-8-azaspiro[4.5]decane-8-sulfonyl fluoride was prepared following the general procedure. An average of two independent experiments was used to calculate the yield (92% and 83%, average: 88%). Physical State: white solid, $^1$H NMR: (400 MHz, CDCl$_3$) δ 3.98 (s, 4 H), 3.59 (t, J=4 Hz, 4 H), 1.83 (t, J=4 Hz, 4 H), $^{13}$C NMR: (101 MHz, CDCl$_3$) δ 105.41, 64.60, 45.66 (d, J=2.0 Hz), 33.96 (d, J=2.0 Hz), $^{19}$F NMR: (376 MHz, CDCl$_3$) δ 42.20 (s, 1 F), MS: (EI) 225.1 [M]+.

Example 19

Di(prop-2-yn-1-yl)sulfamoyl fluoride

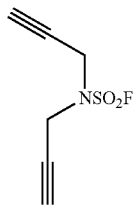

Di(prop-2-yn-1-yl)sulfamoyl fluoride was prepared following the general procedure. An average of two independent experiments was used to calculate the yield (77% and 74%, average: 76%). Physical State: colorless oil, $^1$H NMR: (400 MHz, CDCl$_3$) δ 4.30 (t, J=2.1 Hz, 4H), 2.46 (t, J=2.3 Hz, 2H), $^{13}$C NMR: (101 MHz, CDCl$_3$) δ 75.51 (d, J=1.5 Hz, 1C), 74.68 (d, J=2.2 Hz, 1C), 37.79 (d, J=1.5 Hz, 1C), $^{19}$F NMR: (376 MHz, CDCl$_3$) δ 46.79 (s, 1F).

Example 20

(4-Acetamido-2-chlorophenyl)(fluorosulfonyl)sulfamoyl fluoride

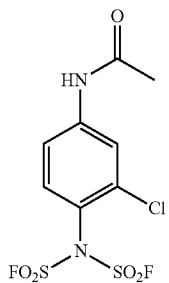

To a reaction mixture of N-(3-chlorophenyl)acetamide (1700 mg, 10.02 mmol) in ClCH$_2$CH$_2$Cl (400 mL) was added Imidodisulfuryl fluoride lithium salt (2830 mg, 15 mmol) and PhI(OAc)$_2$ (4840 mg, 15 mmol), the reaction mixture was stirred at 85° C. for 5 h. The solution was concentrated in vacuo. The residue was purified by column chromatography (80 g silica, 50% ethyl acetate in petroleum ether) to get the title compound as a yellow solid (2300 mg, 66% yield). $^1$H NMR: (400 MHz, DMSO) δ 10.57 (s, 1H), 8.11 (d, J=2.3 Hz, 1H), 8.06 (d, J=8.9 Hz, 1H), 7.67 (dd, J=8.9, 2.3 Hz, 1H), 2.11 (s, 3H). $^{13}$C NMR: (101 MHz, DMSO) δ 169.67 (s, 1H), 168.77 (s, 1H), 144.34 (s, 1H), 137.67 (s, 1H), 133.74 (s, 1H), 132.67 (s, 2H), 131.24 (s, 1H), 126.01 (s, 1H), 123.94 (s, 2H), 123.12 (s, 1H), 120.09 (d, J=17.9 Hz, 5H), 119.09 (s, 2H), 118.77 (s, 2H), 24.26 (s, 2H), 24.04 (s, 2H). $^{19}$F NMR: (376 MHz, DMSO) δ 58.49 (s, 1H).

Example 21

(4-Acetamido-3-chlorophenyl)(fluorosulfonyl)sulfamoyl fluoride

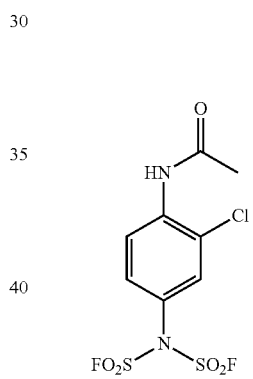

To a reaction mixture of N-(2-chlorophenyl)acetamide (1700 mg, 10.02 mmol) in ClCH$_2$CH$_2$Cl (400 mL) was added Imidodisulfuryl fluoride lithium salt (2830 mg, 15 mmol) and PhI(OAc)$_2$ (4840 mg, 15 mmol), the reaction mixture was stirred at 85° C. for 4 h. The solution was concentrated in vacuo. The residue was purified by column chromatography (80 g silica, 25% ethyl acetate in petroleum ether) to get the title compound as a yellow solid (2900 mg, 83% yield). $^1$H NMR: (400 MHz, DMSO) δ 9.81 (s, 1H), 8.28 (d, J=2.5 Hz, 1H), 8.15-8.07 (m, 1H), 7.87 (dd, J=8.9, 2.5 Hz, 1H), 2.17 (s, 3H). $^{13}$C NMR: (101 MHz, DMSO) δ 169.33 (d, J=7.3 Hz, 17H), 168.99 (s, 12H), 139.14 (d, J=12.1 Hz, 16H), 138.29 (s, 4H), 135.93 (s, 9H), 134.40 (s, 6H), 131.01 (s, 36H), 130.71 (s, 25H), 128.93 (d, J=11.7 Hz, 53H), 127.91 (d, J=17.9 Hz, 33H), 126.12 (d, J=17.1 Hz, 55H), 125.76 (s, 21H), 118.99 (s, 12H), 117.58 (s, 10H), 23.86-23.78 (m, 1H), 23.71 (s, 36H), 23.36 (d, J=30.1 Hz, 39H). $^{19}$F NMR: (376 MHz, DMSO) δ 57.74 (s, 1H).

Example 22

(4-Acetamido-2-(trifluoromethyl)phenyl)(fluorosulfonyl)sulfamoyl fluoride

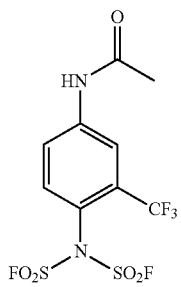

To a reaction mixture of N-(3-(trifluoromethyl)phenyl)acetamide (1500 mg, 7.383 mmol) in ClCH$_2$CH$_2$Cl (400 mL) was added Imidodisulfuryl fluoride lithium salt (2070 mg, 11.1 mmol) and PhI(OAc)$_2$ (3570 mg, 11.1 mmol), the reaction mixture was stirred at 85° C. for 4 h. The solution was concentrated in vacuo. The residue was purified by column chromatography (80 g silica, 30% ethyl acetate in petroleum ether) to get the title compound as a yellow solid (1500 mg, 54% yield). $^1$H NMR: (400 MHz, DMSO) δ 10.75 (s, 1H), 8.31 (d, J=2.3 Hz, 1H), 8.14 (d, J=8.8 Hz, 1H), 8.07 (dd, J=8.9, 2.3 Hz, 1H), 2.13 (s, 3H). $^{13}$C NMR: (101 MHz, DMSO) δ 169.95 (d, J=9.1 Hz, 19H), 169.12 (d, J=9.1 Hz, 13H), 144.00 (d, J=12.3 Hz, 19H), 137.54 (d, J=10.9 Hz, 11H), 133.21 (s, 32H), 132.08 (s, 11H), 128.55 (s, 7H), 128.24 (s, 7H), 126.32 (d, J=5.6 Hz, 22H), 124.85 (s, 3H), 124.14-123.66 (m, 63H), 123.39 (s, 10H), 122.92 (d, J=29.6 Hz, 15H), 122.53-122.49 (m, 1H), 122.17 (d, J=8.3 Hz, 22H), 121.06 (s, 5H), 118.36 (d, J=5.1 Hz, 38H), 116.95 (d, J=5.8 Hz, 27H), 24.45-23.87 (m, 61H). $^{19}$F NMR: (376 MHz, DMSO) δ 56.65-56.46 (m, −1H), −60.02 (t, J=5.1 Hz, 1H).

Example 23

4-Cyanophenyl sulfurofluoridate

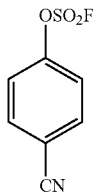

To a 2-dram vial containing 4-hydroxybenzonitrile (50 mg, 0.42 mmol) and (4-acetamidophenyl)(fluorosulfonyl)sulfamoyl fluoride (158 mg, 0.50 mmol) in tetrahydrofuran (2 mL), and 2,3,4,6,7,8,9,10-octahydropyrimido[1,2-a]azepine (141 mg, 0.92 mmol) was added and the reaction solution was stirred at room temperature for 10 min. The mixture was diluted with ethyl acetate (2×10 ml) and washed with brine (10 ml). The organic fraction was dried with Na$_2$SO$_4$ and concentrated under reduced pressure. The residue was purified by column chromatography (4 g silica, 40% ethyl acetate in petroleum ether) to get the title compound as a colorless oil (83 mg, 99% yield). $^1$H NMR: (400 MHz, DMSO) δ 8.13 (dd, J=9.2, 2.3 Hz, 2H), 7.88 (d, J=8.3 Hz, 2H). $^{13}$C NMR: (101 MHz, DMSO) δ 152.02 (s, 1H), 135.37 (s, 6H), 122.64 (s, 6H), 117.40 (s, 1H), 112.49 (s, 1H). $^{19}$F NMR: (376 MHz, DMSO) δ 40.19-40.08 (m, 1H).

Example 24

6-Methylpyridin-3-yl sulfurofluoridate

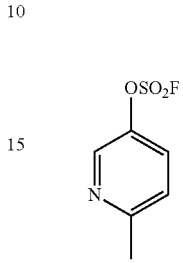

To a 2-dram vial containing 6-methylpyridin-3-ol (50 mg, 0.46 mmol) and (4-acetamidophenyl)(fluorosulfonyl)sulfamoyl fluoride (173 mg, 0.55 mmol) in tetrahydrofuran (2 mL), 2,3,4,6,7,8,9,10-octahydropyrimido[1,2-a]azepine (153 mg, 1.01 mmol) was added and the reaction solution was stirred at room temperature for 15 min. The mixture was diluted with ethyl acetate (2×10 ml) and washed with brine (10 ml). The organic fraction was dried with Na$_2$SO$_4$ and concentrated under reduced pressure. The residue was purified by column chromatography (4 g silica, 19% ethyl acetate in petroleum ether) to get the title compound as a white solid (86 mg, 99% yield). $^1$H NMR: (400 MHz, DMSO) δ 8.73 (d, J=2.8 Hz, 1H), 8.02 (dd, J=8.6, 2.9 Hz, 1H), 7.51 (d, J=8.7 Hz, 1H), 2.54 (s, 3H). $^{13}$C NMR: (101 MHz, DMSO) δ 159.36 (s, 1H), 145.33 (s, 1H), 141.54 (s, 3H), 129.42 (s, 3H), 124.84 (s, 3H), 23.48 (s, 3H). $^{19}$F NMR: (376 MHz, DMSO) δ 38.93 (s, 1H).

Example 25

4-Cyano-3-(trifluoromethyl)phenyl sulfurofluoridate

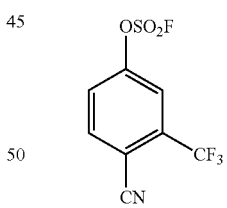

To a 2-dram vial containing 4-hydroxy-2-(trifluoromethyl)benzonitrile (50 mg, 0.27 mmol) and (4-acetamidophenyl)(fluorosulfonyl)sulfamoyl fluoride (101 mg, 0.321 mmol) in dichloromethane (5 mL), and triethylamine (81 mg, 0.802 mmol) was added and the reaction solution was stirred at room temperature for 20 hour. The mixture was diluted with ethyl acetate (2×10 ml) and washed with brine (10 ml). The organic fraction was dried with Na$_2$SO$_4$ and concentrated under reduced pressure. The residue was purified by column chromatography (4 g silica, 27% ethyl acetate in petroleum ether) to get the title compound as a colorless oil (62 mg, 83% yield). $^1$H NMR: (400 MHz, DMSO) δ 8.48 (dd, J=5.3, 2.9 Hz, 2H), 8.27 (dd, J=8.6, 2.0 Hz, 1H). $^{13}$C NMR: (101 MHz, DMSO) δ 151.58 (s, 27H), 138.59 (s, 73H), 126.81 (s, 72H), 122.90 (s, 1H), 121.53 (d, J=4.6 Hz, 38H), 114.37 (s, 21H), 109.74 (d, J=2.1 Hz, 12H). $^{19}$F NMR: (376 MHz, DMSO) δ 41.22 (s, 1H), −60.93 (s, 2H).

Example 26

4-(2-Chlorodibenzo[b,f][1,4]oxazepin-11-yl)piperazine-1-sulfonyl fluoride

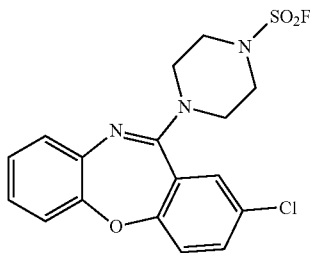 [SMILES: O=S(=O)(F)N1CCN(C2=Nc3ccccc3Oc3ccc(Cl)cc32)CC1]

To a 2-dram vial containing 2-chloro-11-(piperazin-1-yl)dibenzo[b,f][1,4]oxazepine (50 mg, 0.16 mmol) and (4-acetamidophenyl)(fluorosulfonyl)sulfamoyl fluoride (60 mg, 0.191 mmol) in dimethyl sulfoxide (5 mL), potassium carbonate (66 mg, 0.478 mmol) was added and the reaction solution was stirred at room temperature for 1 hour. The mixture was diluted with ethyl acetate (2×10 ml) and washed with brine (10 ml). The organic fraction was dried with Na$_2$SO$_4$ and concentrated under reduced pressure. The residue was purified by column chromatography (4 g silica, 15% ethyl acetate in petroleum ether) to get the title compound as a white solid (56 mg, 89% yield). $^1$H NMR: (400 MHz, DMSO) δ 7.66 (dd, J=8.7, 2.5 Hz, 1H), 7.59 (d, J=2.5 Hz, 1H), 7.43 (d, J=8.7 Hz, 1H), 7.22 (d, J=8.0 Hz, 1H), 7.16-7.00 (m, 3H), 3.61 (s, 8H). $^{13}$C NMR: (101 MHz, DMSO) δ 158.76 (s, 2H), 157.96 (s, 2H), 151.26 (s, 2H), 139.33 (s, 1H), 133.38 (s, 5H), 129.81 (s, 3H), 128.87 (s, 5H), 126.57 (s, 5H), 125.92 (s, 5H), 124.88 (s, 5H), 124.09 (s, 2H), 123.17 (s, 5H), 120.30 (s, 5H), 45.97 (d, J=60.0 Hz, 26H). $^{19}$F NMR: (376 MHz, DMSO) δ 40.10 (s, 1H).

Example 27

4-Benzoylphenyl sulfurofluoridate

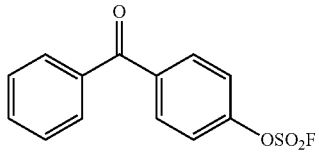

To a 2-dram vial containing (4-hydroxyphenyl)(phenyl)methanone (50 mg, 0.25 mmol) and (4-acetamidophenyl)(fluorosulfonyl)sulfamoyl fluoride (95 mg, 0.303 mmol) in dimethyl sulfoxide (5 mL), potassium carbonate (105 mg, 0.757 mmol) was added and the reaction solution was stirred at room temperature for 1 hour. The mixture was diluted with ethyl acetate (2×10 ml) and washed with brine (10 ml). The organic fraction was dried with Na$_2$SO$_4$ and concentrated under reduced pressure. The residue was purified by column chromatography (4 g silica, 15% ethyl acetate in petroleum ether) to get the title compound as a white solid (53 mg, 75% yield). $^1$H NMR: (400 MHz, DMSO) δ 7.99-7.90 (m, 2H), 7.85-7.75 (m, 4H), 7.72 (t, J=7.4 Hz, 1H), 7.59 (t, J=7.6 Hz, 2H). $^{13}$C NMR: (101 MHz, DMSO) δ 194.24 (s, 1H), 151.80 (s, 1H), 137.66 (s, 1H), 136.26 (s, 1H), 133.12 (s, 3H), 132.20 (s, 6H), 129.75 (s, 6H), 128.65 (s, 6H), 121.39 (s, 6H). $^{19}$F NMR: (376 MHz, DMSO) δ 39.59 (s, 1H).

Example 28

4-Benzoylphenyl sulfurofluoridate (Synthesized with DBU

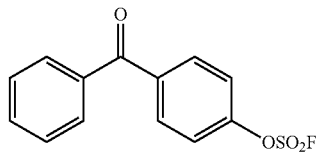

To a 2-dram vial containing (4-hydroxyphenyl)(phenyl)methanone (79.3 mg, 0.4 mmol) and (4-acetamidophenyl)(fluorosulfonyl)sulfamoyl fluoride (151 mg, 0.48 mmol) in tetrahydrofuran (2 mL), 2,3,4,6,7,8,9,10-octahydropyrimido[1,2-a]azepine (134 mg, 0.88 mmol) was added and the reaction solution was stirred at room temperature for 10 minutes. The mixture was diluted with ethyl acetate (2×10 ml) and washed with brine (10 ml). The organic fraction was dried with Na$_2$SO$_4$ and concentrated under reduced pressure. The residue was purified by automated column chromatography (4 g silica, 15% ethyl acetate in petroleum ether) yielding product as a white solid (110 mg, 98% yield).

Example 29

2-Oxo-2H-chromen-7-yl sulfurofluoridate

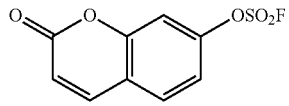

To a 2-dram vial containing 7-hydroxy-2H-chromen-2-one (50 mg, 0.31 mmol) and (4-acetamidophenyl)(fluorosulfonyl)sulfamoyl fluoride (116 mg, 0.37 mmol) in dimethyl sulfoxide (4 mL), potassium carbonate (128 mg, 0.925 mmol) was added and the reaction solution was stirred at room temperature for 1 hour. The mixture was diluted with ethyl acetate (2×10 ml) and washed with brine (10 ml). The organic fraction was dried with Na$_2$SO$_4$ and concentrated under reduced pressure. The residue was purified by column chromatography (4 g silica, 15% ethyl acetate in petroleum ether) to get product as a white solid (63 mg, 84% yield). $^1$H NMR: (400 MHz, DMSO) δ 8.13 (d, J=9.6 Hz, 1H), 7.96 (d, J=8.6 Hz, 1H), 7.86 (d, J=2.3 Hz, 1H), 7.66-7.59 (m, 1H), 6.61 (d, J=9.6 Hz, 1H). $^{13}$C NMR: (101 MHz, DMSO) δ 159.10 (s, 1H), 154.09 (s, 1H), 150.56 (s, 1H), 143.15 (s, 3H), 130.63 (s, 3H), 119.46 (s, 1H), 117.40 (d, J=9.6 Hz, 6H), 110.11 (s, 3H). $^{19}$F NMR: (376 MHz, DMSO) δ 39.76 (s, 1H).

Example 30

5-Chloroquinolin-8-yl sulfurofluoridate

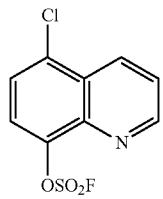

To a 2-dram vial containing 5-chloroquinolin-8-ol (50 mg, 0.28 mmol) and (4-acetamidophenyl)(fluorosulfonyl)sulfamoyl fluoride (105 mg, 0.334 mmol) in dimethyl sulfoxide (4 mL), potassium carbonate (115 mg, 0.835 mmol) was added and the reaction solution was stirred at room temperature for 1 hour. The mixture was diluted with ethyl acetate (2×10 ml) and washed with brine (10 ml). The organic fraction was dried with $Na_2SO_4$ and concentrated under reduced pressure. The residue was purified by automated column chromatography (4 g silica, 20% ethyl acetate in petroleum ether) to get product as a white solid (69 mg, 95% yield). $^1$H NMR: (400 MHz, DMSO) δ 9.19 (dd, J=4.2, 1.3 Hz, 1H), 8.70 (d, J=8.6 Hz, 1H), 8.14 (d, J=8.4 Hz, 1H), 7.98 (d, J=8.4 Hz, 1H), 7.90 (dd, J=8.6, 4.2 Hz, 1H). $^{13}$C NMR: (101 MHz, DMSO) δ 153.01 (s, 4H), 144.06 (s, 1H), 139.92 (s, 1H), 133.05 (d, J=6.8 Hz, 4H), 131.13 (s, 1H), 126.99 (s, 1H), 126.55 (s, 4H), 124.37 (s, 4H), 122.29 (s, 4H). $^{19}$F NMR: (376 MHz, DMSO) δ 41.98 (s, 83H).

Example 31

4-(Hydroxydiphenylmethyl)piperidine-1-sulfonyl fluoride

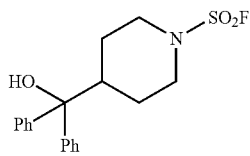 [SMILES: O=S(=O)(F)N1CCC(C(O)(c2ccccc2)c2ccccc2)CC1]

To a 2-dram vial containing diphenyl(piperidin-4-yl)methanol (50 mg, 0.19 mmol) and (4-acetamidophenyl)(fluorosulfonyl)sulfamoyl fluoride (70.5 mg, 0.224 mmol) in dichloromethane (4 mL) and water (1 ml), magnesium oxide (38 mg, 0.935 mmol) and N,N-dimethylpyridin-4-amine (23 mg, 0.187) was added and the reaction solution was stirred at room temperature for 1 hour. The mixture was diluted with dichloromethane (2×10 ml) and washed with brine (10 ml). The organic fraction was dried with $Na_2SO_4$ and concentrated under reduced pressure. The residue was purified by column chromatography (4 g silica, 18% ethyl acetate in petroleum ether) to get product as a white solid (59 mg, 90% yield). $^1$H NMR: (400 MHz, DMSO) δ 7.53 (d, J=7.6 Hz, 4H), 7.28 (t, J=7.7 Hz, 4H), 7.14 (t, J=7.3 Hz, 2H), 5.48 (s, 1H), 3.80 (d, J=12.5 Hz, 2H), 3.14 (t, J=12.7 Hz, 2H), 2.85 (t, J=11.6 Hz, 1H), 1.54 (ddd, J=16.0, 13.2, 3.9 Hz, 2H), 1.40 (d, J=12.8 Hz, 2H). $^{13}$C NMR: (101 MHz, DMSO) δ 146.74 (s, 1H), 127.95 (s, 4H), 126.04 (s, 2H), 125.63 (s, 4H), 78.39 (s, 1H), 47.27 (s, 2H), 41.66 (s, 1H), 25.11 (s, 2H). $^{19}$F NMR: (376 MHz, DMSO) δ 41.17 (s, 1H). HRMS (ESI+): Calculated for $[C_{18}H_{20}FNO_3S+Na]^+$, 372.41; found, 372.7.

Example 32

4-Aminophenyl sulfurofluoridate

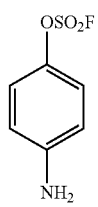

To a 2-dram vial containing 4-aminophenol (50 mg, 0.46 mmol) and (4-acetamidophenyl)(fluorosulfonyl)sulfamoyl fluoride (173 mg, 0.55 mmol) in tetrahydrofuran (2 mL), 2,3,4,6,7,8,9,10-octahydropyrimido[1,2-a]azepine (153 mg, 1.01 mmol) was added and the reaction solution was stirred at room temperature for 10 minutes. The mixture was diluted with ethyl acetate (2×10 ml) and washed with brine (10 ml). The organic fraction was dried with $Na_2SO_4$ and concentrated under reduced pressure. The residue was purified by column chromatography (4 g silica, 30% ethyl acetate in petroleum ether) to get product as a yellow oil (83 mg, 95% yield). $^1$H NMR: (400 MHz, DMSO) δ 7.16 (d, J=8.9 Hz, 2H), 6.72-6.51 (m, 2H), 5.52 (s, 2H). $^{13}$C NMR: (101 MHz, DMSO) δ 149.42 (s, 1H), 139.94 (s, 1H), 121.43 (s, 5H), 114.09 (s, 5H). $^{19}$F NMR: (376 MHz, DMSO) δ 36.32 (s, 1H).

Example 33

Propane-2,2-diylbis(4,1-phenylene) bis(sulfurofluoridate)

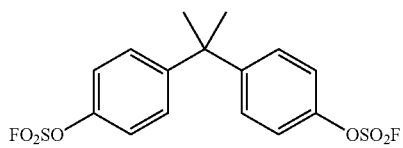

Propane-2,2-diylbis(4,1-phenylene) bis(sulfurofluoridate) was prepared following the general procedure using 4,4'-(propane-2,2-diyl)diphenol with the exception of 2.2 equiv. of AISF and 3.2 equiv. of DBU employed in the reaction. An average of two independent experiments was used to calculate the yield reported in the manuscript (93% and 95%, average: 94%). $^1$H NMR: (400 MHz, CDCl$_3$) δ 7.33 (d, J=9.1 Hz, 4 H), 7.28 (d, J=8.9 Hz, 4 H), 1.72 (s, 6 H). $^{13}$C NMR: (101 MHz, CDCl$_3$) δ 150.41, 148.21, 128.71, 120.58 (d, J=1.0 Hz), 42.93, 30.73. $^{19}$F NMR: (376 MHz, CDCl$_3$) δ 37.52 (s, 2 F). MS: (EI) 392.1 [M]+.

Example 34

Mesityl sulfurofluoridate

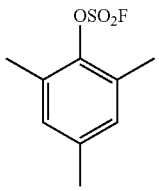

To a 2-dram vial containing 2,4,6-trimethylphenol (50 mg, 0.37 mmol) and (4-acetamidophenyl)(fluorosulfonyl)sulfamoyl fluoride (138 mg, 0.441 mmol) in tetrahydrofuran (2 mL), 2,3,4,6,7,8,9,10-octahydropyrimido[1,2-a]azepine (123 mg, 0.808 mmol) was added and the reaction solution was stirred at room temperature for 10 minutes. The mixture was diluted with ethyl acetate (2×10 ml) and washed with brine (10 ml). The organic fraction was dried with $Na_2SO_4$ and concentrated under reduced pressure. The residue was purified by column chromatography (4 g silica, 0% ethyl acetate in petroleum ether) to get product as a colorless oil (71 mg, 89% yield). $^1$H NMR: (400 MHz, DMSO) δ 7.08 (s, 2H), 2.27 (d, J=8.3 Hz, 9H). $^{13}$C NMR: (101 MHz, DMSO) δ 146.33 (d, J=1.2 Hz, 1H), 138.19 (s, 2H), 130.44 (s, 9H), 129.83 (s, 4H), 20.16 (s, 4H), 15.76 (d, J=2.7 Hz, 8H). $^{19}$F NMR: (376 MHz, DMSO) δ 43.59 (s, 1H).

Example 35

4-Formyl-2-methoxyphenyl sulfurofluoridate

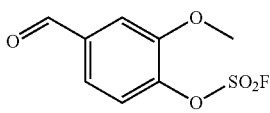

To a 2-dram vial containing 4-hydroxy-3-methoxybenzaldehyde (50 mg, 0.33 mmol) and (4-acetamidophenyl)(fluorosulfonyl)sulfamoyl fluoride (124 mg, 0.394 mmol) in tetrahydrofuran (2 mL), 2,3,4,6,7,8,9,10-octahydropyrimido[1,2-a]azepine (110 mg, 0.723 mmol) was added and the reaction solution was stirred at room temperature for 5 minutes. The mixture was diluted with ethyl acetate (2×10 ml) and washed with brine (10 ml). The organic fraction was dried with $Na_2SO_4$ and concentrated under reduced pressure. The residue was purified by column chromatography (4 g silica, 26% ethyl acetate in petroleum ether) to get product as a colorless oil (75 mg, 97% yield). $^1$H NMR: (400 MHz, DMSO) δ 10.03 (s, 1H), 7.96-7.76 (m, 2H), 7.68 (d, J=8.3 Hz, 1H), 4.01 (s, 3H). $^{13}$C NMR: (101 MHz, DMSO) δ 191.85 (s, 3H), 151.23 (s, 1H), 141.74 (s, 1H), 137.32 (s, 1H), 123.40 (s, 3H), 123.18 (s, 3H), 113.72 (s, 3H), 56.78 (s, 3H). $^{19}$F NMR: (376 MHz, DMSO) δ 41.70 (s, 1H).

Example 36

Di(prop-2-yn-1-yl)sulfamoyl fluoride

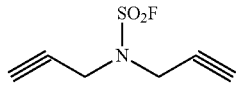

To a 2-dram vial containing di(prop-2-yn-1-yl)amine (50 mg, 0.54 mmol) and (4-acetamidophenyl)(fluorosulfonyl)sulfamoyl fluoride (202 mg, 0.644 mmol) in tetrahydrofuran (2 mL), 2,3,4,6,7,8,9,10-octahydropyrimido[1,2-a]azepine (180 mg, 1.18 mmol) was added and the reaction solution was stirred at room temperature for 2 hour. (4-acetamidophenyl)(fluorosulfonyl)sulfamoyl fluoride (102 mg, 0.322 mmol) was added the solution, the reaction mixture was stirred at room temperature for 1 h. The mixture was diluted with ethyl acetate (2×10 ml) and washed with brine (10 ml). The organic fraction was dried with $Na_2SO_4$ and concentrated under reduced pressure. The residue was purified by column chromatography (4 g silica, 2-10% ethyl acetate in petroleum ether) to get product as a colorless oil (70 mg, 74% yield). 1H NMR: (400 MHz, $CDCl_3$) δ 4.30 (t, J=2.0 Hz, 2H), 2.46 (t, J=2.3 Hz, 1H). $^{19}$F NMR: (376 MHz, $CDCl_3$) δ 46.78 (s, 1H).

Example 37

1,4-Dioxa-8-azaspiro[4.5]decane-8-sulfonyl fluoride

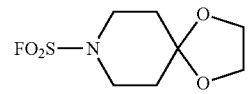

To a 2-dram vial containing 1,4-dioxa-8-azaspiro[4.5]decane (48 mg, 0.34 mmol) and (4-acetamidophenyl)(fluorosulfonyl)sulfamoyl fluoride (126 mg, 0.402 mmol) in tetrahydrofuran (2 mL), 2,3,4,6,7,8,9,10-octahydropyrimido[1,2-a]azepine (112 mg, 0.738 mmol) was added and the reaction solution was stirred at room temperature for 10 minutes. The mixture was diluted with ethyl acetate (2×10 ml) and washed with brine (10 ml). The organic fraction was dried with $Na_2SO_4$ and concentrated under reduced pressure. The residue was purified by column chromatography (4 g silica, 18% ethyl acetate in petroleum ether) to get product as a white solid (63 mg, 83% yield). $^1$H NMR: (400 MHz, DMSO) δ 3.92 (s, 4H), 3.59-3.46 (m, 4H), 1.86-1.71 (m, 4H). $^{13}$C NMR: (101 MHz, DMSO) δ 104.79 (s, 1H), 64.03 (s, 4H), 45.64 (d, J=1.0 Hz, 4H), 33.35 (s, 4H). $^{19}$F NMR: (376 MHz, DMSO) δ 43.00 (s, 1H).

Example 38

(2,2-Dimethoxyethyl)(methyl)sulfamoyl fluoride

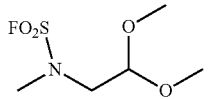

To a 2-dram vial containing 2,2-dimethoxy-N-methyl-ethan-1-amine (50 mg, 0.42 mmol) and (4-acetamidophenyl)(fluorosulfonyl)sulfamoyl fluoride (158 mg, 0.504 mmol) in tetrahydrofuran (2 mL), 2,3,4,6,7,8,9,10-octahydropyrimido[1,2-a]azepine (141 mg, 0.923 mmol) was added and the reaction solution was stirred at room temperature for 10 minutes. The mixture was diluted with ethyl acetate (2×10 ml) and washed with brine (10 ml). The organic fraction was dried with $Na_2SO_4$ and concentrated under reduced pressure. The residue was purified by column chromatography (4 g silica, 15-30% dichloromethane in petroleum ether) to get product as a colorless oil (62 mg, 73% yield). $^1$H NMR: (400 MHz, DMSO) δ 4.58 (t, J=5.3 Hz, 1H), 3.42 (dd, J=5.3, 2.1 Hz, 2H), 3.33 (s, 6H), 3.06 (d, J=2.3 Hz, 3H). $^{13}$C NMR: (101 MHz, DMSO) δ 101.29 (d, J=2.6 Hz, 1H), 54.13 (s, 2H), 51.92 (d, J=2.2 Hz, 1H), 37.11 (d, J=1.4 Hz, 1H). $^{19}$F NMR: (376 MHz, DMSO) δ 44.43 (s, 1H).

Example 39

Quinazolin-4-yl sulfurofluoridate

To a 2-dram vial containing quinazolin-4-o (50 mg, 0.34 mmol) and (4-acetamidophenyl)(fluorosulfonyl)sulfamoyl fluoride (129 mg, 0.411 mmol) in dimethyl sulfoxide (5 mL), potassium carbonate (142 mg, 1.03 mmol) was added and the reaction solution was stirred at room temperature for 1 hour. The mixture was diluted with ethyl acetate (2×10 ml) and washed with brine (10 ml). The organic fraction was dried with $Na_2SO_4$ and concentrated under reduced pressure. The residue was purified by automated column chromatography (4 g silica, 18% ethyl acetate in petroleum ether) yielding product as a white solid (10 mg, 13% yield). $^1$H NMR: (400 MHz, DMSO) δ 8.50 (s, 1H), 8.25 (dd, J=7.9, 1.1 Hz, 1H), 8.04-7.96 (m, 1H), 7.79 (d, J=7.9 Hz, 1H), 7.71 (t, J=7.6 Hz, 1H). $^{19}$F NMR: (376 MHz, DMSO) δ 53.93-53.80 (m, 7H), 50.45 (s, 1H).

Example 40

Quinazolin-4-yl sulfurofluoridate (Synthesized with DBU)

To a 2-dram vial containing quinazolin-4-o (100 mg, 0.68 mmol) and (4-acetamidophenyl)(fluorosulfonyl)sulfamoyl fluoride (258 mg, 0.822 mmol) in tetrahydrofuran (10 mL), 2,3,4,6,7,8,9,10-octahydropyrimido[1,2-a]azepine (229 mg, 1.50 mmol) was added and the reaction solution was stirred at room temperature for 2 hour. The mixture was diluted with ethyl acetate (2×20 ml) and washed with brine (20 ml). The organic fraction was dried with $Na_2SO_4$ and concentrated under reduced pressure. The residue was purified by column chromatography (12 g silica, 18% ethyl acetate in petroleum ether) to get product as a white solid (30 mg, 19.2% yield).

Example 41

3,5-Bis((fluorosulfonyl)oxy)benzoic acid

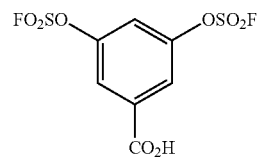

3,5-Bis((fluorosulfonyl)oxy)benzoic acid was prepared following the general procedure using 3,5-dihydroxybenzoic acid with the exceptions that 3.2 equiv. of AISF and 4.2 equiv. of DBU were employed in the reaction. An average of two independent experiments was used to calculate the yield (82% and 87%, average: 85%). Physical State: white solid. $^1$H NMR: (400 MHz, $CDCl_3$) δ 9.55 (br s, 1 H), 8.18 (s, 2 H), 7.67 (s, 1 H). $^{13}$C NMR: (101 MHz, $CDCl_3$) δ 167.63, 149.93, 133.63, 123.10, 120.07. $^{19}$F NMR: (376 MHz, $CDCl_3$) δ 39.64 (s, 1 F). MS: (ESI) 317.0 [M–H]$^-$.

Example 42

2-Oxo-3-(((2R,3S,4R,5R,6S)-3,4,5-trihydroxy-6-(hydroxymethyl)tetra-hydro-2H-pyran-2-yl)oxy)-2H-chromen-7-yl sulfurofluoridate

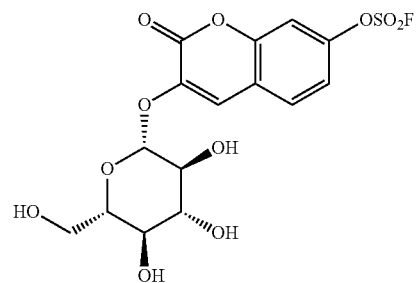

2-Oxo-3-(((2R,3S,4R,5R,6S)-3,4,5-trihydroxy-6-(hydroxymethyl)tetra-hydro-2H-pyran-2-yl)oxy)-2H-chromen-7-yl sulfurofluoridate was prepared according to the following procedure. To a two-dram vial containing esculin hydrate (68.1 mg, 0.2 mmol) in anhydrous DMSO (2 mL) was added AISF (75.4 mg, 0.24 mmol, 1.2 equiv.) followed by cesium carbonate (143.0 mg, 0.44 mmol, 2.2 equiv.) in one portion. The reaction stirred at room temperature for 1 hour. The crude reaction was filtered, and purified by reversed-phase column chromatography on Waters Sunfire C18 column with water/acetonitrile gradient over a period of 19 minutes (flow rate=25 mL/min). The purified fractions were combined and extracted with ethyl acetate (2×10 mL). The ethyl acetate fractions were combined, dried with anhydrous sodium sulfate and filtered. The filtrate was concentrated under reduced pressure to obtain a single diastereomer of the title compound as a white solid. An average of two independent experiments was used to calculate the yield reported in the manuscript (55% and 58%, average: 57%). Physical State: white solid. $^1$H NMR: (400 MHz, DMSO-d$_6$) δ 8.04 (d, J=9.7 Hz, 1 H), 7.95 (s, 1 H), 7.79 (s, 1H), 6.65 (d, J=9.6 Hz, 1 H), 5.40 (d, J=5.1 Hz, 1 H), 5.16 (d, J=4.6 Hz, 1 H), 5.12 (d, J=5.3 Hz, 1 H), 5.09 (d, J=7.2 Hz, 1 H), 4.61 (t, J=5.8 Hz, 1 H), 3.75 (dd, J=12.0, 5.6 Hz, 1 H), 3.53 (dt, J=11.7, 5.9 Hz, 1 H), 3.45 (dd, J=9.2, 5.5 Hz, 1 H), 3.34-3.20 (m, 3 H). $^{13}$C NMR: (101 MHz, DMSO-d$_6$) δ 160.23, 148.66, 145.89, 144.10, 140.69, 120.57, 118.89, 116.71, 112.53, 101.83, 78.27, 77.77, 74.01, 70.38, 61.42. $^{19}$F NMR: (376 MHz, DMSO-d$_6$) δ 42.81 (s, 1 F). MS: (ESI) 440.2 [M+H$_2$O]$^+$.

Example 43

3,5-Bis((fluorosulfonyl)oxy)benzoic acid

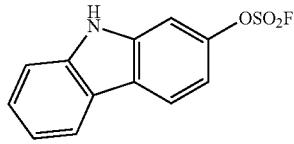

9H-Carbazol-2-yl sulfurofluoridate was prepared according to the following procedure. A two-dram vial containing 2-hydroxycarbazole (73 mg, 0.40 mmol) and AISF (131 mg, 0.417 mmol, 1.04 equiv.) in THF (2 mL) was cooled in an ice bath. To this solution was added DBU (134 mg, 0.880 mmol, 2.2 equiv.) over a period of 30 seconds. TLC (25% EtOAc/heptane) after 5 minutes indicated consumption of 2-hydroxycarbazole and formation of a higher R$_f$ product. The mixture was diluted with EtOAc (20 mL) and washed with water (15 mL) and brine (10 mL). The organic fraction was dried with anhydrous MgSO$_4$, filtered and concentrated under reduced pressure. The crude residue was purified by silica gel flash chromatography (diethyl ether/pentane) to afford the title compound as a white solid. An average of two independent experiments was used to calculate the yield reported in the manuscript (72% and 76%, average: 74%). X-ray quality crystals obtained by slow evaporation from CH$_2$Cl$_2$. Physical State: white solid. $^1$H NMR: (400 MHz, CDCl$_3$) δ 8.24 (br s, 1H), 8.12 (d, J=9.0 Hz, 1H), 8.09 (d, J=7.8 Hz, 1H), 7.51-7.46 (m, 2H), 7.43 (d, J=2.0 Hz, 1H), 7.34-7.29 (m, 1H), 7.24-7.20 (m, 1H). $^{13}$C NMR: (101 MHz, CDCl$_3$) δ 148.2, 140.3, 139.2, 126.8, 123.5, 122.2, 121.5, 120.6, 120.4, 112.1, 110.9, 103.4. $^{19}$F NMR: (376 MHz, CDCl$_3$) δ 37.0 (s, 1F). HRMS: Calculated for C$_{12}$H$_9$FNO$_3$S [M+H]+266.0282, found 266.0276. IR (neat): v=1604, 1441, 1229, 1211, 1106, 958, 894, 823, 754, 728 cm$^{-1}$. mp: 171-172° C.

Example 44

9-(Fluorosulfonyl)-9H-carbazol-2-yl sulfurofluoridate

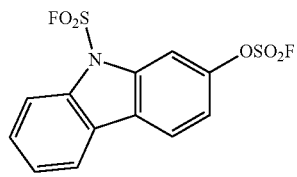

9-(Fluorosulfonyl)-9H-carbazol-2-yl sulfurofluoridate was prepared following the general procedure using 2-hydroxycarbazole with the exception that 2.2 equiv. of AISF and 4.4 equiv. of DBU were employed in the reaction. An average of two independent experiments was used to calculate the yield reported in the manuscript (65% and 69%, average: 67%). Physical State: white solid. $^1$H NMR: (400 MHz, CDCl$_3$) δ 8.13-8.09 (m, 3H), 8.06 (d, J=7.8 Hz, 1H), 7.64 (td, J=8.2, 1.2 Hz, 1H), 7.56 (t, J=7.4 Hz, 1H), 7.52 (dd, J=8.6, 1.6 Hz, 1H). $^{13}$C NMR: (101 MHz, CDCl$_3$) δ 149.0, 138.2, 137.5, 129.1, 126.4, 125.9, 124.7, 121.7, 120.8, 118.3, 114.8, 108.7. $^{19}$F NMR: (376 MHz, CDCl$_3$) δ 53.9 (s, 1F), 38.2 (s, 1F). MS: (EI) 347.0 [M]+.

Example 45

Ethyl 4-(phenylamino)benzoate

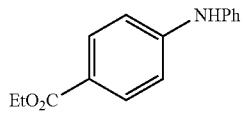

Ethyl 4-(phenylamino)benzoate was prepared according to the following procedure. A two-dram vial containing ethyl 4-hydroxybenzoate (70.0 mg, 0.420 mmol), AISF (159.0 mg, 0.51 mmol), aniline (78.5 mg, 77 μL, 0.84 mmol), cesium carbonate (412 mg, 1.26 mmol), Cp(cinnamyl)-Pd (3.0 mg, 0.01 mmol) and xantphos (7.3 mg, 0.012 mmol) was purged with nitrogen and then THF (2 mL, purged with nitrogen for 15 minutes) was added. The reaction mixture was stirred at room temperature for 1 hour and then heated to 60° C. for 17 hours. The reaction was cooled to room temperature and partitioned between CH$_2$Cl$_2$ and brine. The aqueous layer was extracted with CH$_2$Cl$_2$ (2×) and the organic extracts were combined and dried with anhydrous sodium sulfate, filtered and concentrated under reduced pressure. The crude residue was purified by silica gel chromatography (0-20% MTBE/hexanes) to afford the title compound as a colorless oil (95 mg, 94% yield). Physical State: colorless oil. $^1$H NMR: (400 MHz, CDCl$_3$) δ 7.93 (d, J=8.7 Hz, 2 H), 7.34 (t, J=7.9 Hz, 2 H), 7.17 (d, J=7.6 Hz, 2 H), 7.06 (t, J=7.4 Hz, 1 H), 6.99 (d, J=8.8 Hz, 2 H), 6.05 (s, 1 H), 4.34 (q, J=7.1 Hz, 2 H), 1.38 (t, J=7.1 Hz, 3 H). $^{13}$C NMR: (101 MHz, CDCl$_3$) δ 166.48, 147.91, 140.89, 131.39, 129.46, 122.99, 121.47, 120.29, 114.59, 60.42, 14.40. MS: (ESI) 242.2 [M+H]+.

Example 46

Ethyl [1,1'-biphenyl]-4-carboxylate

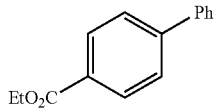

Ethyl [1,1'-biphenyl]-4-carboxylate was prepared according to the following procedure. A two-dram vial containing ethyl 4-hydroxybenzoate (68 mg, 0.41 mmol), AISF (154 mg, 0.49 mmol), phenylboronic acid (100 mg, 0.82 mmol), cesium carbonate (400 mg, 1.23 mmol), Pd(OAc)$_2$ (2.3 mg, 0.01 mmol) and triphenylphosphine (5.4 mg, 0.021 mmol) was purged with nitrogen and then THF (2 mL, purged with nitrogen for 15 minutes) was added. The reaction mixture was stirred at room temperature for 1 hour and then water (0.4 mL, purged with nitrogen for 15 minutes) was added and the reaction was heated to 60° C. for 4 hours. The reaction was cooled to room temperature and partitioned between CH$_2$Cl$_2$ and brine. The aqueous layer was extracted with CH$_2$Cl$_2$ (2×) and the organic extracts were combined and dried with anhydrous sodium sulfate, filtered and concentrated under reduced pressure. The crude residue was purified by silica gel chromatography (0-20% MTBE/hexanes) to afford the title compound as a white solid (89 mg, 96% yield). Physical State: white solid. $^1$H NMR: (400 MHz, CDCl$_3$) δ 8.12 (d, J=8.3 Hz, 2 H), 7.66 (d, J=8.3 Hz, 2 H), 7.63 (d, J=7.4 Hz, 2 H), 7.47 (t, J=7.5 Hz, 2 H), 7.40 (t, J=7.3 Hz, 1 H), 4.41 (q, J=7.1 Hz, 2 H), 1.42 (t, J=7.1 Hz, 3 H). $^{13}$C NMR: (101 MHz, CDCl$_3$) δ 166.50, 145.50, 140.04, 130.03, 129.23, 128.89, 128.08, 127.25, 126.98, 60.95, 14.35. MS: (ESI) 227.1 [M+H]$^+$.

Example 47

Ethyl 4-(3-hydroxy-3-methylbut-1-yn-1-yl)benzoate

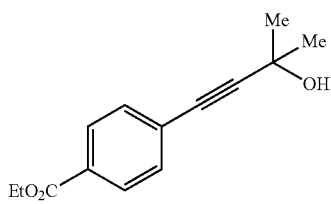 [SMILES: CCOC(=O)c1ccc(C#CC(C)(C)O)cc1]

Ethyl 4-(3-hydroxy-3-methylbut-1-yn-1-yl)benzoate was prepared according to the following procedure. A two-dram vial containing ethyl 4-hydroxybenzoate (66.5 mg, 0.4 mmol), AISF (151 mg, 0.48 mmol), 2-methyl-3-butyn-2-ol (50.5 mg, 0.6 mmol), copper iodide (7.6 mg, 0.04 mmol), Cp(cinnamyl)-Pd (2.3 mg, 0.008 mmol), triphenylphosphine (6.3 mg, 0.024 mmol) and DBU (183 mg, 179 uL, 1.20 mmol) was purged with nitrogen and then DMF (2 mL, purged with nitrogen for 15 minutes) was added. The reaction was stirred at room temperature for 15 hours. The reaction was partitioned between CH$_2$Cl$_2$ and brine. The aqueous layer was extracted with CH$_2$Cl$_2$ (2×) and the organic extracts were combined and dried with anhydrous sodium sulfate, filtered and concentrated under reduced pressure. The crude residue was purified by silica gel chromatography (0-20% MTBE/hexanes) to afford was prepared according to the following procedure. as a colorless oil (65 mg, 70% yield). Physical State: colorless oil. $^1$H NMR: (400 MHz, CDCl$_3$) δ 7.97 (d, J=8.5 Hz, 2 H), 7.46 (d, J=8.5 Hz, 2 H), 4.37 (q, J=7.1 Hz, 2 H), 2.13 (s, 1 H), 1.63 (s, 3 H), 1.39 (t, J=7.1 Hz, 3 H). $^{13}$C NMR: (101 MHz, CDCl$_3$) δ 166.05, 131.49, 129.88, 129.35, 127.32, 96.61, 81.48, 65.61, 61.14, 31.35, 14.29. MS: (EI) 232.2 [M]$^+$.

Example 48

5-Chloroquinolin-8-yl (4-(methylamino)phenyl) sulfate

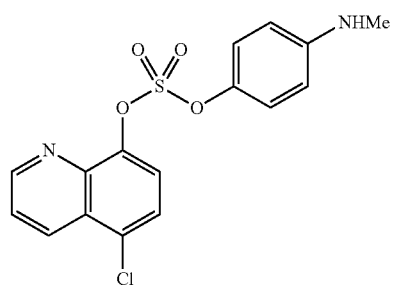 [SMILES: CNc1ccc(OS(=O)(=O)Oc2ccc(Cl)c3cccnc23)cc1]

5-Chloroquinolin-8-yl (4-(methylamino)phenyl) sulfate was prepared according to the following procedure. A two-dram vial containing 5-chloro-8-hydroxy-quinoline (72 mg, 0.40 mmol), 4-(tert-butyldimethylsilyloxy)-N-methylaniline (124 mg, 0.521 mmol), and AISF (151 mg, 0.481 mmol) was purged with nitrogen and then acetonitrile (2 mL, purged with nitrogen for 15 minutes) was added, followed by DBU (134 mg, 132 µL, 0.882 mmol) over a period of 30 seconds. The reaction was stirred at room temperature for 2 hours. The reaction was partitioned between EtOAc and brine. The aqueous layer was extracted with EtOAc (2×) and the organic extracts were combined and dried with anhydrous sodium sulfate, filtered and concentrated under reduced pressure. The crude residue was purified by silica gel chromatography (EtOAc/heptane) to afford the title compound as a white solid (131 mg, 90% yield). Physical State: white solid. $^1$H NMR: (400 MHz, CDCl$_3$) δ 9.07 (dd, J=4.2, 1.6 Hz, 1 H), 8.57 (dd, J=8.6, 1.6 Hz, 1 H), 7.61-7.55 (m, 3 H), 7.31 (d, J=9.0 Hz, 2 H), 6.57 (d, J=9.0 Hz, 2 H), 3.87 (s, 1 H), 2.82 (s, 3 H). $^{13}$C NMR: (101 MHz, CDCl$_3$) δ 151.79, 148.57, 145.52, 141.72, 141.49, 133.00, 130.29, 127.50, 125.85, 122.96, 122.32, 121.00, 112.45, 30.73. MS: (ESI) 365.1 [M+H]+.

Example 49

1-Benzyl-1H-benzo[d][1,2,3]triazole

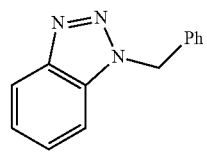 [SMILES: c1ccc(Cn2nnc3ccccc32)cc1]

1-Benzyl-1H-benzo[d][1,2,3]triazole was prepared according to the following procedure. A two-dram vial containing 2-trimethylsilyl phenol (100 mg, 0.6 mmol), AISF (201 mg, 0.64 mmol), benzyl azide (53 mg, 50.0 µL, 0.40 mmol), cesium carbonate (390 mg, 1.2 mmol) and 18-crown-6 (106 mg, 0.4 mmol) was purged with nitrogen and then acetonitrile (2 mL, purged with nitrogen for 15 minutes) was added. The reaction was stirred at 40° C. for 15 hours. The reaction was cooled to room temperature and partitioned between ether and brine. The aqueous layer was extracted with ether (2×) and the organic extracts were combined and dried with anhydrous sodium sulfate, filtered and concentrated under reduced pressure. The crude residue was purified by silica gel chromatography (ether/pentane) to afford the title compound as a white solid (68 mg, 81% yield). Physical State: white solid. $^1$H NMR: (400 MHz, CDCl$_3$) δ 8.01 (d, J=8.0 Hz, 1 H), 7.36-7.20 (m, 8 H), 5.79 (s, 2H). $^{13}$C NMR: (101 MHz, CDCl$_3$) δ 146.33, 134.73, 132.77, 128.98, 128.44, 127.55, 127.37, 123.88, 120.07, 109.69, 52.25. MS: (ESI) 210.2 [M+H]+.

What is claimed is:

1. A compound of Formula I:

(I)

wherein Ar is a moiety of Formula II:

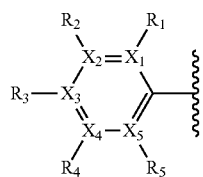

(II)

wherein:
each of $X_1$, $X_2$, $X_3$, $X_4$, and $X_5$ is carbon;
each of $R_1$, $R_2$, $R_4$, and $R_5$ is independently selected from hydrogen, halide, an optionally substituted alkyl, an optionally substituted aryl, an optionally substituted five-membered heteroaryl, or an optionally substituted six-membered heteroaryl, or a moiety of formula $R_6$—C(=O)-NH-$\xi$, wherein $R_6$ is selected from hydrogen, an optionally substituted alkyl, an optionally substituted aryl, an optionally substituted five-membered heteroaryl, or an optionally substituted six-membered heteroaryl;

$R_3$ is selected from halide, an optionally substituted aryl, an optionally substituted five-membered heteroaryl, or an optionally substituted six-membered heteroaryl, or a moiety of formula $R_6$—C(=O)—NH—$\xi$, wherein $R_6$ is selected from hydrogen, an optionally substituted alkyl, an optionally substituted aryl, an optionally substituted five-membered heteroaryl, or an optionally substituted six-membered heteroaryl.

2. The compound of claim 1, wherein each of $R_1$, $R_2$, $R_4$, and $R_5$ is independently selected from hydrogen, halide, an optionally substituted alkyl, an optionally substituted aryl, an optionally substituted five-membered heteroaryl, or an optionally substituted six-membered heteroaryl.

3. The compound of claim 1, wherein $R_3$ is a moiety of formula $R_6$—C(=O)—NH—$\xi$.

4. The compound of claim 1, wherein each of $R_1$, $R_2$, $R_4$, and $R_5$ is independently selected from hydrogen, fluoro, chloro, bromo, methyl, trifluoromethyl, ethyl, perfluoroethyl, n-propyl, i-propyl, n-butyl, sec-butyl, or tert-butyl.

5. The compound of claim 1, wherein each of $R_1$, $R_2$, $R_4$, and $R_5$ is independently selected from hydrogen, chloro, methyl, trifluoromethyl, and ethyl.

6. The compound of claim 1, wherein $R_1$, $R_2$, $R_4$, and $R_5$ are hydrogen.

7. The compound of claim 1, wherein $R_6$ is independently selected from hydrogen, methyl, ethyl, n-propyl, i-propyl, n-butyl, sec-butyl, or tert-butyl.

8. The compound of claim 1, wherein $R_6$ is independently selected from methyl, ethyl, and n-propyl.

9. The compound of claim 1, wherein $R_6$ is methyl.

10. The compound of claim 1, wherein the compound is a compound of Formula III

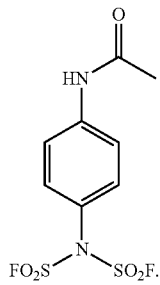

(III)

* * * * *